United States Patent
Kamiya et al.

(10) Patent No.: US 10,016,506 B2
(45) Date of Patent: Jul. 10, 2018

(54) METHOD FOR PRODUCING HYDROGEL, METHOD FOR ENVELOPING ENVELOPMENT TARGET, AND METHOD FOR RELEASING ENVELOPMENT TARGET

(71) Applicants: Noriho Kamiya, Fukuoka (JP); Kosuke Moriyama, Fukuoka (JP); Hitachi, Ltd, Tokyo (JP)

(72) Inventors: Noriho Kamiya, Fukuoka (JP); Kosuke Moriyama, Fukuoka (JP); Kosuke Minamihata, Fukuoka (JP)

(73) Assignees: Hitachi, Ltd., Tokyo (JP); Noriho Kamiya, Fukuoka (JP); Kosuke Moriyama, Fukuoka (JP)

(*) Notice: Subject to any disclaimer, the term of this patent is extended or adjusted under 35 U.S.C. 154(b) by 0 days.

(21) Appl. No.: 15/304,675

(22) PCT Filed: Apr. 16, 2015

(86) PCT No.: PCT/JP2015/062458
§ 371 (c)(1),
(2) Date: Oct. 17, 2016

(87) PCT Pub. No.: WO2015/159995
PCT Pub. Date: Oct. 22, 2015

(65) Prior Publication Data
US 2017/0239356 A1  Aug. 24, 2017

(30) Foreign Application Priority Data

Apr. 17, 2014 (JP) ................. 2014-085790
Dec. 4, 2014 (JP) ................. 2014-245478

(51) Int. Cl.
*A61K 47/34* (2017.01)
*C08G 75/14* (2006.01)
*C12P 11/00* (2006.01)

(52) U.S. Cl.
CPC .............. *A61K 47/34* (2013.01); *C08G 75/14* (2013.01); *C12P 11/00* (2013.01); *C12Y 111/01007* (2013.01); *C08G 2210/00* (2013.01)

(58) Field of Classification Search
None
See application file for complete search history.

(56) References Cited

U.S. PATENT DOCUMENTS

| | | |
|---|---|---|
| 2004/0225077 A1 | 11/2004 | Gravett et al. |
| 2011/0280914 A1 | 11/2011 | Prestwich et al. |
| 2014/0329267 A1 | 11/2014 | Odriozola et al. |

FOREIGN PATENT DOCUMENTS

| | | | |
|---|---|---|---|
| EP | 2597110 A1 | 8/2010 | |
| EP | 2597110 A1 * | 5/2013 | ............ C08G 65/326 |

(Continued)

OTHER PUBLICATIONS

Singh et al. (Embedding of Active Proteins and Living Cells in Redox-Sensitive Hydrogels and Nanogels through Enzymatic Cross-linking, Angew. Chem Int. Ed. 2013, 52, 3000-3003).*

(Continued)

*Primary Examiner* — Robert A Wax
*Assistant Examiner* — Melissa S Mercier
(74) *Attorney, Agent, or Firm* — Cooper & Dunham LLP

(57) ABSTRACT

Provided is a method for producing a hydrogel, which enables a hydrogel comprising polyethylene glycol to be produced under low peroxidase concentration conditions and physiological conditions. The method for producing a hydrogel involves crosslinking polyethylene glycol having two or more thiol groups using peroxidase in the presence of a phenol compound.

7 Claims, 17 Drawing Sheets

(56) References Cited

FOREIGN PATENT DOCUMENTS

| | | |
|---|---|---|
| JP | 2005-200494 A | 7/2005 |
| JP | 2011-173887 A | 9/2011 |
| WO | WO2010/087912 A1 | 8/2010 |

OTHER PUBLICATIONS

Goldman et al. (Reduction of Phenoxyl Radicals by Thioredoxin Results in Selective Oxidation of its SH-Groups to Disulfides. An antioxidant function of Thioreodixin; Biochemistry 1995, 34, 4765-4772).*

International Preliminary Report on Patentability (and English translation) in connection with PCT/JP2015/062458.

Josefa Hernandez-Ruiz et al. "Catalase-like activity of horseradish peoxidase: relationship to enzyme inactivation by $H_2O_2$", Biochem. J., 2001, 354, pp. 107-114.

Shinji Sakai et al. "Glucose-triggered co-enzymatic hydrogelation of aqueous polymer solutions", RSC Advances, 2012, 2, pp. 1502-1507.

Smriti Singh et al. "Embedding of Active Proteins and Living Cells in Redox-Sensitive Hydrogels and Nanogels through Enzymatic Cross-Linking", Angew. Chem. Int. Ed. 2013, 52, pp. 3000-3003.

C. Obinger et al. "Generation of Hydrogen Peroxide by Plant Peroxidases Mediated Thiol Oxidation", Phyton, 1997, 37, pp. 219-226.

Lisa K. Folkes et al. "Kinetics of reduction of tyrosine phenoxyl radicals by glutathione", Arch. Biochem. Biophys., 2011, 506, pp. 242-249.

Smriti Singh et al, "Embedding of Active proteins and Living Cells in Redox-Sensitive Hydrogels and Nanogels through Enzymatic Cross-Linking", Chem, Int. Ed., 2013, vol. 52, pp. 3000-3003.

Detcho A. Stoyanovsky et al. "Phenoxyl Radical-Induced Thiol-Dependent Generation of Reactive Oxygen Species: Implications for Benzene Toxicity", Archives of Biochemistry and Biophsics. 1995, vol. 317, No. 2, pp. 315-323.

Radoslav Goldman et al. "Reduction of Phenoxyl Radiacals by Thioredoxin Results in Selective Oxidation of Its SH-Group to Disulfides. An Antioxidant Function of Thioredoxin", Biochemistry, 1995, vol. 34, pp. 4765-4472.

Larry J Kricka et al. "Synthesis and Characterization of 4-Iodophenyiboronic Acid: Anew Enhancer for the Horseradish Peroxidase-Catalyzed Chemiluminescent Oxidation of Luminol", Analytical Biochemistry, 1996, vol. 240, pp. 119-125.

\* cited by examiner

SEQUENCE LISTING

```
<160> NUMBER OF SEQ ID NOS: 4

<210> SEQ ID NO 1
<211> LENGTH: 140
<212> TYPE: PRT
<213> ORGANISM: Artificial Sequence
<220> FEATURE:
<223> OTHER INFORMATION: synthetic

<400> SEQUENCE: 1

Met His His His His His Cys Ala Glu Ala Gly Ile Thr Gly Thr
1               5                   10                  15

Trp Tyr Asn Gln Leu Gly Ser Thr Phe Ile Val Thr Ala Gly Ala Asp
            20                  25                  30

Gly Ala Leu Thr Gly Thr Tyr Glu Ser Ala Val Gly Asn Ala Glu Ser
        35                  40                  45

Arg Tyr Val Leu Thr Gly Arg Tyr Asp Ser Ala Pro Ala Thr Asp Gly
    50                  55                  60

Ser Gly Thr Ala Leu Gly Trp Thr Val Ala Trp Lys Asn Asn Tyr Arg
65                  70                  75                  80
```

```
Asn Ala His Ser Ala Thr Thr Trp Ser Gly Gln Tyr Val Gly Gly Ala
                85                  90                  95

Glu Ala Arg Ile Asn Thr Gln Trp Leu Leu Thr Ser Gly Thr Thr Glu
            100                 105                 110

Ala Asn Ala Trp Lys Ser Thr Leu Val Gly His Asp Thr Phe Thr Lys
        115                 120                 125

Val Lys Pro Ser Ala Ala Ser Gly Gly Gly Tyr
    130                 135                 140

<210> SEQ ID NO 2
<211> LENGTH: 135
<212> TYPE: PRT
<213> ORGANISM: Artificial Sequence
<220> FEATURE:
<223> OTHER INFORMATION: synthetic

<400> SEQUENCE: 2

Met His His His His His Cys Ala Glu Ala Gly Ile Thr Gly Thr
1               5                   10                  15

Trp Tyr Asn Gln Leu Gly Ser Thr Phe Ile Val Thr Ala Gly Ala Asp
            20                  25                  30

Gly Ala Leu Thr Gly Thr Tyr Glu Ser Ala Val Gly Asn Ala Glu Ser
        35                  40                  45

Arg Tyr Val Leu Thr Gly Arg Tyr Asp Ser Ala Pro Ala Thr Asp Gly
    50                  55                  60

Ser Gly Thr Ala Leu Gly Trp Thr Val Ala Trp Lys Asn Asn Tyr Arg
65                  70                  75                  80

Asn Ala His Ser Ala Thr Thr Trp Ser Gly Gln Tyr Val Gly Gly Ala
                85                  90                  95

Glu Ala Arg Ile Asn Thr Gln Trp Leu Leu Thr Ser Gly Thr Thr Glu
            100                 105                 110

Ala Asn Ala Trp Lys Ser Thr Leu Val Gly His Asp Thr Phe Thr Lys
        115                 120                 125

Val Lys Pro Ser Ala Ala Ser
    130                 135

<210> SEQ ID NO 3
<211> LENGTH: 5805
<212> TYPE: DNA
<213> ORGANISM: Artificial Sequence
<220> FEATURE:
<223> OTHER INFORMATION: synthetic

<400> SEQUENCE: 3
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180 gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
```

```
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct aacgtgagt tttcgttcca ctgagcgtca gaccccgtag aaaagatcaa   1620
aggatcttct tgagatcctt ttttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatgaaaaaa   2220
cgccagcaac gcggcctttt tacggttcct ggccttttgc tggccttttg ctcacatgtt   2280
ctttcctgcg ttatccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaagggg atttctgttc atggggtaa   2880 tgataccgat gaaacgagag aggatgctca cgatacgggt tactgatgat gaacatgccc   2940
```

```
ggttactgga acgttgtgag ggtaaacaac tggcggtatg gatgcggcgg gaccagagaa       3000
aaatcactca gggtcaatgc cagcgcttcg ttaatacaga tgtaggtgtt ccacagggta       3060
gccagcagca tcctgcgatg cagatccgga acataatggt gcagggcgct gacttccgcg       3120
tttccagact ttacgaaaca cggaaaccga agaccattca tgttgttgct caggtcgcag       3180
acgttttgca gcagcagtcg cttcacgttc gctcgcgtat cggtgattca ttctgctaac       3240
cagtaaggca accccgccag cctagccggg tcctcaacga caggagcacg atcatgcgca       3300
cccgtggggc cgccatgccg gcgataatgg cctgcttctc gccgaaacgt tggtggcgg        3360 gaccagtgac gaaggcttga gcgagggcgt gcaagattcc gaataccgca agcgacaggc       3420
cgatcatcgt cgcgctccag cgaaagcggt cctcgccgaa aatgacccag agcgctgccg       3480
gcacctgtcc tacgagttgc atgataaaga agacagtcat aagtgcgcg acgatagtca        3540 tgccccgcgc ccaccggaag gagctgactg ggttgaaggc tctcaagggc atcggtcgag       3600
atcccggtgc ctaatgagtg agctaactta cattaattgc gttgcgctca ctgcccgctt       3660
tccagtcggg aaacctgtcg tgccagctgc attaatgaat cggccaacgc gcggggagag       3720
gcggtttgcg tattgggcgc cagggtggtt tttcttttca ccagtgagac gggcaacagc       3780
tgattgccct tcaccgcctg gccctgagag agttgcagca agcggtccac gctggtttgc       3840
cccagcaggc gaaaatcctg tttgatggtg gttaacggcg ggatataaca tgagctgtct       3900
tcggtatcgt cgtatcccac taccgagata tccgcaccaa cgcgcagccc ggactcggta       3960
atggcgcgca ttgcgcccag cgccatctga tcgttggcaa ccagcatcgc agtgggaacg       4020
atgccctcat tcagcatttg catggtttgt tgaaaaccgg acatggcact ccagtcgcct       4080
tcccgttccg ctatcggctg aatttgattg cgagtgagat atttatgcca gccagccaga       4140
cgcagacgcg ccgagacaga acttaatggg cccgctaaca gcgcgatttg ctggtgaccc       4200
aatgcgacca gatgctccac gcccagtcgc gtaccgtctt catgggagaa aataatactg       4260
ttgatgggtg tctggtcaga gacatcaaga ataacgccg gaacattagt gcaggcagct       4320
tccacagcaa tggcatcctg gtcatccagc ggatagttaa tgatcagccc actgacgcgt       4380
tgcgcgagaa gattgtgcac cgccgcttta caggcttcga cgccgcttcg ttctaccatc       4440
gacaccacca cgctggcacc cagttgatcg gcgcgagatt taatcgccgc gacaatttgc       4500
gacggcgcgt gcagggccag actggaggtg caacgccaa tcagcaacga ctgtttgccc        4560
gccagttgtt gtgccacgcg gttgggaatg taattcagct ccgccatcgc cgcttccact       4620
ttttcccgcg ttttcgcaga aacgtggctg gcctggttca ccacgcggga aacggtctga       4680
taagagacac cggcatactc tgcgacatcg tataacgtta ctggtttcac attcaccacc       4740
ctgaattgac tctcttccgg gcgctatcat gccataccgc gaaaggtttt gcgccattcg       4800
atggtgtccg ggatctcgac gctctccctt atgcgactcc tgcattagga agcagcccag       4860
tagtaggttg aggccgttga gcaccgccgc cgcaaggaat ggtgcatgca aggagatggc       4920
gcccaacagt cccccggcca cggggcctgc caccataccc acgccgaaac aagcgctcat       4980
gagcccgaag tggcgagccc gatcttcccc atcggtgatg tcggcgatat aggcgccagc       5040
aaccgcacct gtggcgccgg tgatgccggc cacgatgcgt ccggcgtaga ggatcgagat       5100
ctcgatcccg cgaaattaat acgactcact ataggggaat tgtgagcgga taacaattcc       5160
cctctagaaa taattttgtt taactttaag aaggagatat acatatgcac catcaccacc       5220
atcactgcgc ggaagccggt atcacgggaa cctggtataa tcagctgggg tctactttta       5280
tcgtgacagc aggagcggat ggggcccctga caggtacgta tgagagtgcc gttggtaacg       5340
```

| | |
|---|---|
| cagaatcacg ttatgtcctg actgggcgct acgactccgc tccggcgaca gatggatccg | 5400 |
| ggactgccct gggctggacg gtagcatgga aaataacta tcgtaatgct cacagcgcga | 5460 |
| ccacttggtc tggtcaatac gtgggggcg ccgaggctcg catcaataca cagtggctgc | 5520 |
| tgacgagtgg tacaactgag gcaaatgcgt ggaaatcaac actggttggg catgacacct | 5580 |
| tcacgaaggt caaaccgtca gctgcttcag gtggtggcgg ttactagaag cttgcggccg | 5640 |
| cactcgagca ccaccaccac caccactgag atccggctgc taacaaagcc cgaaaggaag | 5700 |
| ctgagttggc tgctgccacc gctgagcaat aactagcata ccccttggg gcctctaaac | 5760 |
| gggtcttgag gggttttttg ctgaaaggag gaactatatc cggat | 5805 |

<210> SEQ ID NO 4
<211> LENGTH: 5790
<212> TYPE: DNA
<213> ORGANISM: Artificial Sequence
<220> FEATURE:
<223> OTHER INFORMATION: synthetic

<400> SEQUENCE: 4

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tcccttagg | 180 |
| gttccgattt agtgctttac ggcacctcga ccccaaaaaa cttgattagg gtgatggttc | 240 |
| acgtagtggg ccatcgccct gatagacggt ttttcgccct tgacgttgg agtccacgtt | 300 |
| ctttaatagt ggactcttgt tccaaactgg aacaacactc aaccctatct cggtctattc | 360 |
| ttttgattta tagggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg agacaataac cctgataaat gcttcaataa tattgaaaaa ggaagagtat | 600 |
| gagtattcaa catttccgtg tcgccctat tccctttttt gcggcatttt gccttcctgt | 660 |
| ttttgctcac ccagaaacgc tggtgaaagt aaaagatgct gaagatcagt tgggtgcacg | 720 |
| agtgggttac atcgaactgg atctcaacag cggtaagatc cttgagagtt ttcgccccga | 780 |
| agaacgtttt ccaatgatga gcactttta agttctgcta tgtggcgcgg tattatcccg | 840 |
| tattgacgcc gggcaagagc aactcggtcg ccgcatacac tattctcaga atgacttggt | 900 |
| tgagtactca ccagtcacag aaaagcatct tacggatggc atgacagtaa gagaattatg | 960 |
| cagtgctgcc ataaccatga gtgataacac tgcggccaac ttacttctga caacgatcgg | 1020 |
| aggaccgaag gagctaaccg cttttttgca acatgggg gatcatgtaa ctcgccttga | 1080 |
| tcgttgggaa ccggagctga atgaagccat accaaacgac gagcgtgaca ccacgatgcc | 1140 |
| tgcagcaatg gcaacaacgt tgcgcaaact attaactggc gaactactta ctctagcttc | 1200 |
| ccggcaacaa ttaatagact ggatggaggc ggataaagtt gcaggaccac ttctgcgctc | 1260 |
| ggcccttccg gctggctggt ttattgctga taaatctgga gccggtgagc gtgggtctcg | 1320 |
| cggtatcatt gcagcactgg ggccagatgg taagccctcc cgtatcgtag ttatctacac | 1380 |
| gacgggagt caggcaacta tggatgaacg aaatagacag atcgctgaga taggtgcctc | 1440 |
| actgattaag cattggtaac tgtcagacca agtttactca tatatacttt agattgattt | 1500 |
| aaaacttcat ttttaattta aaaggatcta ggtgaagatc cttttttgata atctcatgac | 1560 |

```
caaaatccct taacgtgagt tttcgttcca ctgagcgtca gaccccgtag aaaagatcaa    1620
aggatcttct tgagatcctt tttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtatttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atggggtaa    2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
```

```
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatgccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact ataggggaat tgtgagcgga taacaattcc    5160
cctctagaaa taattttgtt taactttaag aaggagatat acatatgcac catcaccacc    5220
atcactgcgc ggaagccggt atcacgggaa cctggtataa tcagctgggg tctactttta    5280
tcgtgacagc aggagcggat ggggccctga caggtacgta tgagagtgcc gttggtaacg    5340
cagaatcacg ttatgtcctg actgggcgct acgactccgc tccggcgaca gatggatccg    5400
ggactgccct gggctggacg gtagcatgga aaaataacta tcgtaatgct cacagcgcga    5460
ccacttggtc tggtcaatac gtgggggcg ccgaggctcg catcaataca cagtggctgc    5520
tgacgagtgg tacaactgag gcaaatgcgt ggaaatcaac actggttggg catgacacct    5580
tcacgaaggt caaaccgtca gctgcttcat agaagcttgc ggccgcactc gagcaccacc    5640
accaccacca ctgagatccg gctgctaaca aagcccgaaa ggaagctgag ttggctgctg    5700
ccaccgctga gcaataacta gcataacccc ttggggcctc taaacgggtc ttgaggggtt    5760
ttttgctgaa aggaggaact atatccggat                                     5790
```

METHOD FOR PRODUCING HYDROGEL, METHOD FOR ENVELOPING ENVELOPMENT TARGET, AND METHOD FOR RELEASING ENVELOPMENT TARGET

REFERENCE TO SEQUENCE LISTING

This application incorporates-by-reference nucleotide and/or amino acid sequences which are present in the file named "88990 2nd Substitute_Sequence_Listing.txt" which is 17.9 kilobytes in size, and which was created March 24, 2017 in the IBM-PC machine format, having an operating system compatibility with MS-Windows, which is contained in the text file filed March 24, 2017 as part of this application.

TECHNICAL FIELD

The present invention relates to a method for producing a hydrogel. Further, the present invention also relates to a method for enveloping (encapsulating) an envelopment target such as a cell or a drug using the hydrogel produced in that manner, and a method for releasing the enveloped (encapsulated) envelopment target (target to be encapsulated).

BACKGROUND ART

It could be said that hydrogels that can be prepared under mild conditions for organisms and cells are very attractive materials in the medical field. Methods that utilize an enzyme reaction are attracting considerable attention as techniques for obtaining these types of hydrogels. Among such methods, the development of materials that use an enzyme reaction of horseradish peroxidase (HRP) derived from horseradish in crosslinking reactions between polymers has been widely reported.

HRP is an enzyme that uses hydrogen peroxide as a substrate to catalyze oxidative coupling reactions between phenol, aniline and thiol. The hydrogen peroxide that is generally required for the reaction to proceed is typically supplied by adding a hydrogen peroxide solution. However, in this type of method, it has been reported that because the hydrogen peroxide concentration temporarily reaches a high level within the system, the HRP may become deactivated, resulting in the crosslinking reaction not proceeding satisfactorily (Non-Patent Document 1). Moreover, it is also thought that when a cell or protein is enveloped within the hydrogel, a high concentration of hydrogen peroxide may have an effect on the enveloped structure.

Accordingly, in recent years, new methods for preparing hydrogels have been reported in which the HRP catalytic cycle is proceeded without adding hydrogen peroxide (Non-Patent Documents 2 and 3). In Non-Patent Document 2, a glucose oxidase (GOx) is used, and the hydrogen peroxide generated when the GOx oxidizes glucose is used to proceed the HRP catalytic cycle, thereby succeeding in gelling an aqueous solution of a polymer having introduced phenolic hydroxyl groups. In this method, because the hydrogen peroxide is generated gradually within the system, deactivation of the HRP can be suppressed to a minimum. Further, it is also reported that because the crosslinking density increases in the produced hydrogel, the hydrogel has superior mechanical properties compared with hydrogels produced by conventional methods in which hydrogen peroxide is added.

In Non-Patent Document 3, it is reported that a hydrogel can be produced by the extremely simple method of merely mixing a thiol group (SH)-modified polymer and HRP. This method initially uses the hydrogen peroxide generated by SH self-oxidation to proceed the HRP catalytic cycle and produce a hydrogel. Further, it is thought that because hydrogen peroxide is also produced during the HRP catalytic cycle, there is no need to add hydrogen peroxide to the system, thus providing an extremely simple gel production method. However, in the method of Non-Patent Document 3, a hydrogel cannot be produced under physiological conditions of pH 7.4, and a hydrogel cannot be produced unless the pH is 8.5. Furthermore, other problems arise in that a high concentration of HRP ($>1.4 \times 10^3$ U/mL) and a long gelation time ($>2$ h) are required.

It is thought that the reason for these problems is that the HRP catalytic cycle does not proceed efficiently. FIG. 1 is a diagram from Non-Patent Document 4, and illustrates the catalytic cycle when HRP oxidizes SH. In FIG. 1, the rate constant of reaction 3 (HRP (COMP II)+RSH→HRP ($Fe^{3+}$)+RS) is extremely low at 300 $M^{-1}$ $s^{-1}$, and it is thought that this is the cause of the problems mentioned above.

In Non-Patent Document 4, it is reported that adding homovanillic acid during the HRP SH catalytic cycle accelerates the oxidation of SH. In Non-Patent Document 4, it is suggested that this result is due to an acceleration in the production of thiol radicals by a radical rearrangement reaction from phenoxy radicals produced in the system to thiol radicals (Ph-O+RSH→Ph-OH+RS).

Moreover, in Non-Patent Document 5, it is reported that in a system using tyrosine as a phenol derivative and glutathione (GSH) as a thiol derivative, the rate constant for the radical rearrangement reaction from a phenoxy radical to a thiol radical is approximately $2 \times 10^6$ $M^{-1}$ $s^{-1}$. Further, the rate constant when the activated HRP (HRP (COMP (II)) recognizes phenol (HRP (COMP II)+Ph-OH→HRP ($Fe^{3+}$)+Ph-O) is approximately $10^4$ to $10^6$ $M^{-1}$ $s^{-1}$, indicating that the rate constants in these two reactions are much larger than the rate constant for the direct oxidation reaction of SH by HRP (COMP (II)) (reaction 3 in FIG. 1).

On the other hand, Patent Document 1 discloses a polysaccharide hydrogel that is a condensation polymer of a polysaccharide such as hyaluronic acid and a polymerizable compound, and also discloses a method for producing the polysaccharide hydrogel by binding a polymerizable compound to the polysaccharide using a condensing agent, and then treating the resulting mixture with oxygen to polymerize and cure the compound.

CITATION LIST

Patent Literature

Patent Document 1: JP 2005-200494 A

Non-Patent Literature

Non-Patent Document 1: Hernandez-Ruiz et al., Biochem. J., 2001, 354, p. 107
Non-Patent Document 2: Sakai et al., RSC Adv., 2012, 2, p. 1502
Non-Patent Document 3: Groll et al., Angew. Chem. Int. Ed., 2013, 52, p. 1
Non-Patent Document 4: Obinger et al., Phyton, 1997, 37, p. 219

Non-Patent Document 5: Folkes et al., Arch. Biochem. Biophys., 2011, 506, p. 242

SUMMARY OF INVENTION

Technical Problem

One object of the present invention is to provide a method for producing a hydrogel that enables a hydrogel of a polyethylene glycol to be produced under conditions of low peroxidase concentration and under physiological conditions.

Another object of the present invention is to provide a method for enveloping an envelopment target such as a cell or a drug using the hydrogel produced in the above manner, and a method for releasing the enveloped envelopment target.

Solution to Problem

The present invention provides a method for producing a hydrogel which involves crosslinking a polyethylene glycol having two or more thiol groups using a peroxidase in the presence of a phenol compound. The method is preferably a method for producing a hydrogel by crosslinking a polyethylene glycol having two or more thiol groups using a peroxidase in the presence of a phenol compound without adding hydrogen peroxide.

In the method for producing a hydrogel described above, the peroxidase is preferably a peroxidase derived from horseradish.

In the method for producing a hydrogel described above, the phenol compound is preferably at least one of tyramine hydrochloride, phenol, N-glycyl-L-tyrosine, hydroquinone, resorcinol, catechol and serotonin.

In the method for producing a hydrogel described above, the polyethylene glycol having two or more thiol groups and a thiol compound having one or more thiol groups may be crosslinked using the peroxidase in the presence of the phenol compound.

In the method for producing a hydrogel described above, the polyethylene glycol having two or more thiol groups and a phenol compound having one or more thiol groups may be crosslinked using the peroxidase.

Further, the present invention also provides a method for enveloping an envelopment target which involves producing a hydrogel by crosslinking a polyethylene glycol having two or more thiol groups using a peroxidase in the presence of a phenol compound, and enveloping the envelopment target in the hydrogel.

Furthermore, the present invention also provides a method for releasing an envelopment target which involves releasing an envelopment target, which has been enveloped in a hydrogel by producing a hydrogel by crosslinking a polyethylene glycol having two or more thiol groups using a peroxidase in the presence of a phenol compound and in the presence of the envelopment target, by dissolving the hydrogel using a reducing agent.

Advantageous Effects of the Invention

The present invention enables the production of a hydrogel of a polyethylene glycol under conditions of low peroxidase concentration and under physiological conditions.

Further, the present invention is also able to provide a method for enveloping an envelopment target such as a cell or a drug using the hydrogel produced in the above manner, and a method for releasing the enveloped envelopment target.

Figure 18:
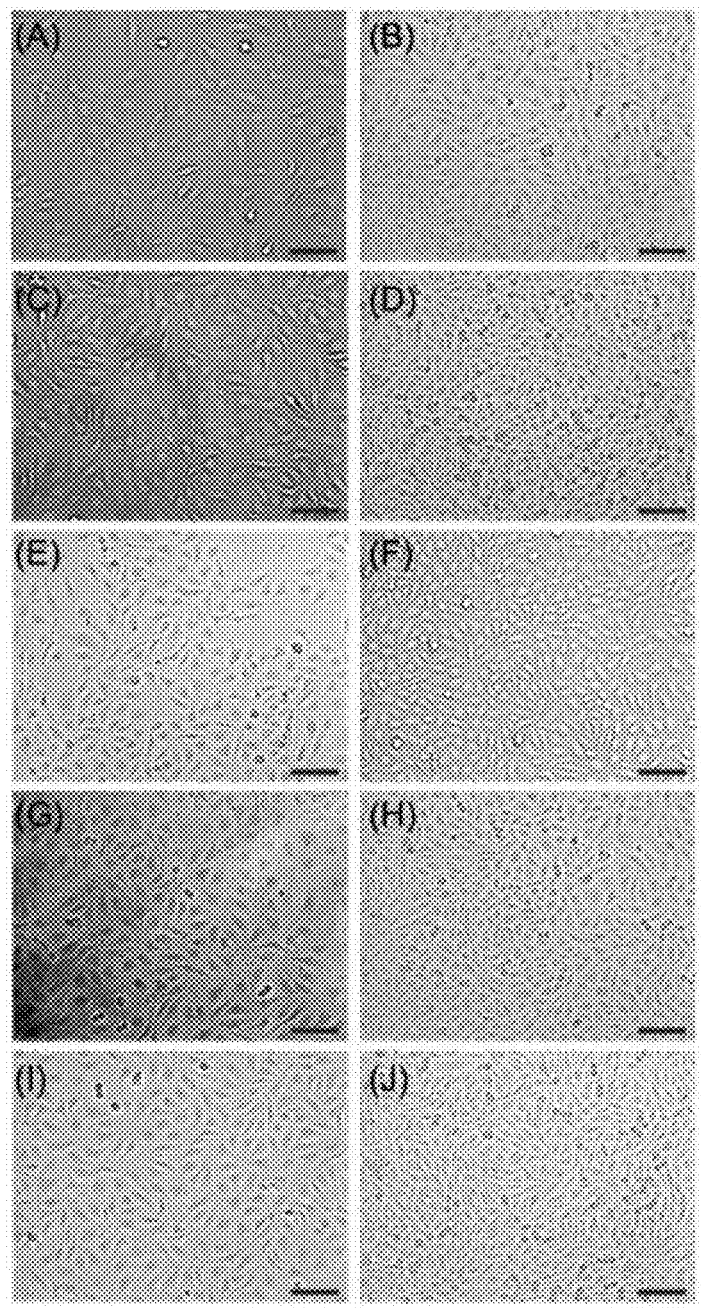

FIG. 18 shows microscope photographs from Example 12 of L929 fibroblasts inoculated on (A, B) P5G0.01, (C, D) P5G0.1, (E, F) P2.5G0.1, (G, H) P10G0.1 and (I, J) a gelatin-coated dish, (A, C, E, G, I) 3 days after inoculation, and (B, D, F, H, J) 5 days after inoculation.

Figure 19:
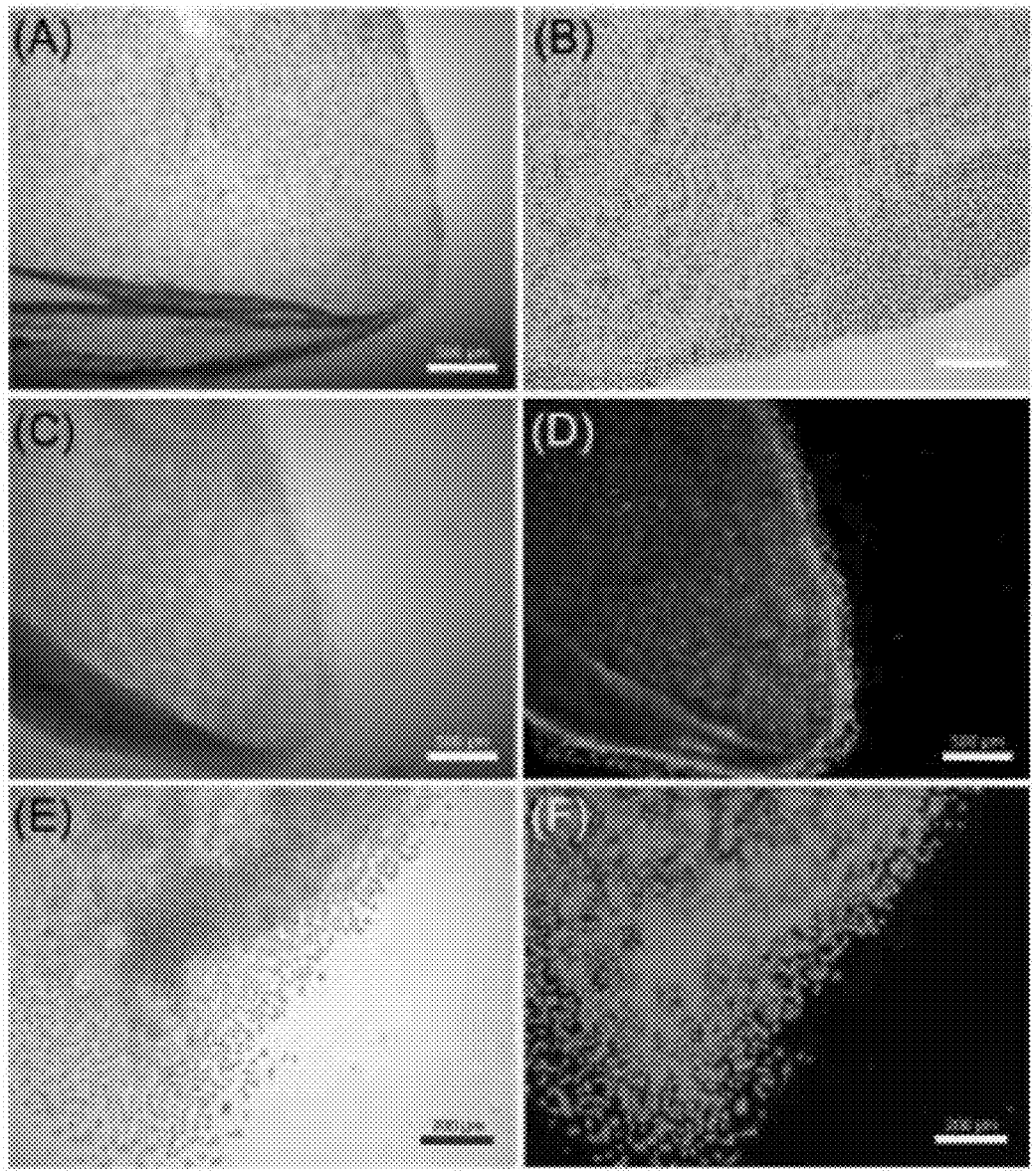

FIG. 19 shows microscope photographs of L929 fibroblast sheets in Example 12. (A) and (B) show cell sheets peeled from a (PEG-SH)-(Gela-SH) hydrogel 30 minutes after the addition of a cysteine solution, and (C) to (F) show the cell sheets 24 hours after transfer to cell culture dishes. (A) to (C) and (E) are bright field images, and (D) and (F) are fluorescence microscope photographs after staining. The lines on the photos indicate 500 μm in (A), (C) and (D), and indicate 200 μm in (B), (E) and (F).

Figure 20:
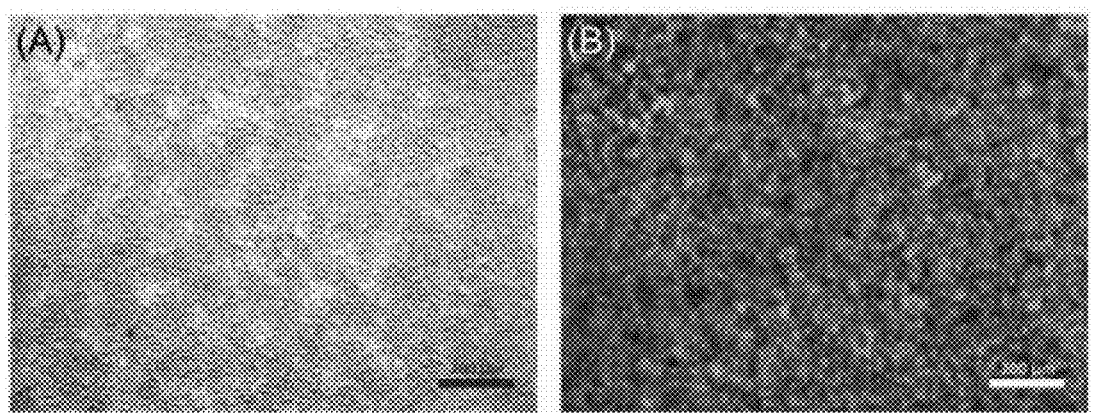

FIG. 20 shows microscope photographs from Example 12 of L929 fibroblast sheets 24 hours after reinoculation on cell culture dishes. (A) shows a bright field image, and (B) shows a fluorescence microscope photograph after staining. The lines on the photographs indicate 200 μm.

DESCRIPTION OF EMBODIMENTS

Embodiments of the present invention are described below. These embodiments are merely examples of implementing the present invention, and the present invention is in no way limited by these embodiments.

As a result of intensive investigation, the inventors of the present invention discovered that by crosslinking a polyethylene glycol having two or more thiol groups using a peroxidase in the presence of a phenol compound, a polyethylene glycol hydrogel could be produced under conditions of low peroxidase concentration and under physiological conditions, even without adding hydrogen peroxide.

There are no particular limitations on the polyethylene glycol having two or more thiol groups, and examples include the polyethylene glycols shown below, having two or more terminals modified by thiol groups. These compounds may be used individually, or combinations of two or more compounds may be used.

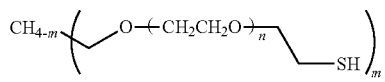

(Each n may be the same or different, and is within a range from 10 to 1,000, and m represents an integer of 2 to 4.)

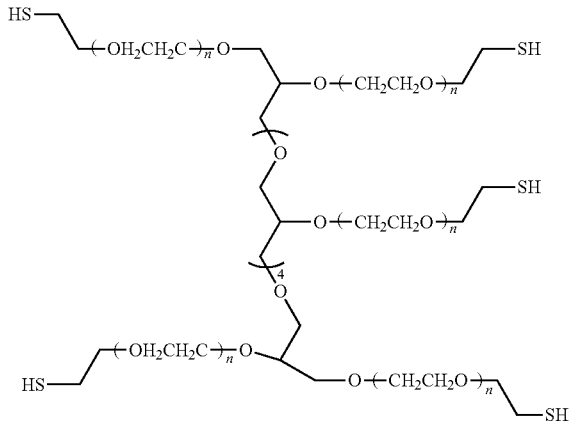

8-arm polyethylene glycol in which the terminals are modified by SH (8-arm PEG-SH) (Each n may be the same or different, and is within a range from 10 to 1,000.)

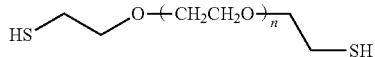

(Each n is within a range from 10 to 1,000.)

Specific examples include the 4-arm polyethylene glycols (4-arm PEG-SH) shown below, having the terminals modified by SH.

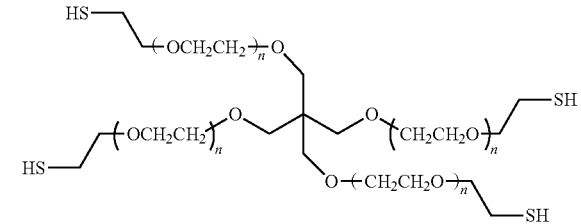

(Each n may be the same or different, and is within a range from 10 to 1,000.)

There are no particular limitations on the phenol compound, provided the compound has a phenol structure, and examples include low-molecular weight phenol compounds having at least 1 but not more than 6 phenolic hydroxyl groups, and having a molecular weight of not more than 500. Specific examples of low-molecular weight phenol compounds having at least 1 but not more than 6 phenolic hydroxyl groups and having a molecular weight of not more than 500 include phenol, 1,2-dihydroxybenzene (catechol), 1,3-dihydroxybenzene (resorcinol), 1,4-dihydroxybenzene (hydroquinone), tyramine and the hydrochloride thereof, serotonin, N-glycyl-L-tyrosine (Gly-Tyr), 5-hydroxyindole-3-acetic acid, 3-(4-hydroxyphenyl)propionic acid, methyl 3-(4-hydroxyphenyl)propionate, 4-hydroxyphenylacetic acid, 3-hydroxyphenylacetic acid, 3,4-dihydroxyphenylacetic acid, 3,4-dihydroxyphenylalanine, 4-hydroxyphenylpyruvic acid, 3-(4-hydroxyphenyl)-1-propanol, 3-(2,4-dihydroxyphenyl)propionic acid, 3,4-dihydroxyhydrocinnamic acid, p-coumaric acid, caffeic acid, dopamine, 6-hydroxydopamine, norepinephrine and benserazide. Of these, at least one compound among tyramine hydrochloride, phenol, N-glycyl-L-tyrosine, hydroquinone, resorcinol, catechol and serotonin is preferred, and in terms of enabling gelation to be achieved in a comparatively short time period, at least one compound among tyramine hydrochloride, phenol, N-glycyl-L-tyrosine, hydroquinone, resorcinol and serotonin is more preferred.

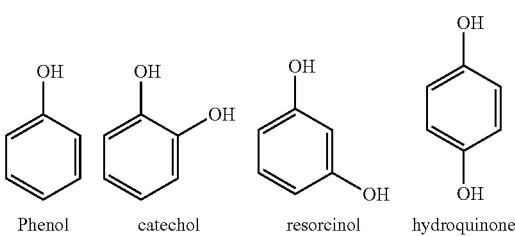

-continued

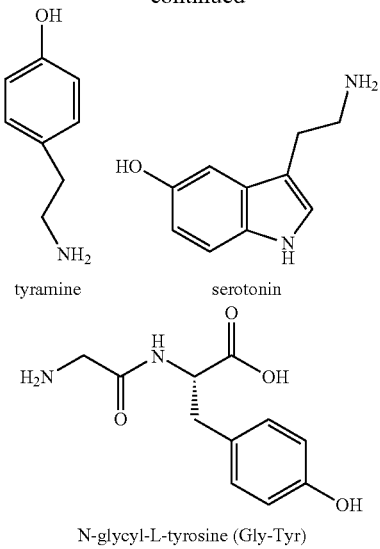

tyramine serotonin

N-glycyl-L-tyrosine (Gly-Tyr)

The amount added of the phenol compound is, for example, within a range from 1/100 equivalents to 20 equivalents relative to the thiol group concentration, and is preferably within a range from 1/10 equivalents to 10 equivalents. If the amount added of the phenol compound is less than 1/100 equivalents relative to the thiol concentration, then the time required for gelation may lengthen, whereas if the amount exceeds 20 equivalents, coupling between molecules of the phenol compound may sometimes proceed preferentially.

Peroxidase is an enzyme that uses hydrogen peroxide as a substrate to catalyze oxidative coupling reactions between phenol, aniline, thiol and the like. There are no particular limitations on the origin of the peroxidase, and examples include cow livers, horse blood cells, human blood cells, *M. lysodeikticus*, horseradish, soybeans, Japanese radishes, turnips, thyroid glands, cows milk, intestines, white blood cells, red blood cells, yeasts, *Caldariomyces fumago*, and *Streptococcus faecalis*. Among these, from the viewpoints of reactivity, stability, and ease of availability and the like, peroxidase derived from horseradish is particularly preferred.

The amount added of the peroxidase, for example as an enzyme concentration within the system, is within a range from 0.1 U/mL to 50 U/mL, and is preferably within a range from 1 U/mL to 10 U/mL. If the amount added of the peroxidase is less than 0.1 U/mL, then the time required for gelation may sometimes lengthen, whereas if the amount exceeds 50 U/mL, then the time required for gelation may lengthen depending on the concentration of the phenol compound within the system.

There are no particular limitations on the reaction solvent, provided the solvent is capable of dissolving the polyethylene glycol having two or more thiol groups, the phenol compound and the peroxidase, and examples include water, phosphate buffered saline (PBS), and cell culture solutions.

Although there are no particular limitations on the amount of the reaction solvent, provided the amount is sufficient to dissolve the polyethylene glycol having two or more thiol groups, the phenol compound and the peroxidase, the amount is typically within a range from 70 to 99 wt %, and preferably within a range from 85 to 95 wt %, relative to the weight of the gelation reaction solution. The minimum amount of solvent required varies depending on the solubility of the polyethylene glycol that is used. Further, if the amount of the reaction solvent exceeds 99 wt %, then gel formation may sometimes become difficult.

The pH during the reaction is, for example, within a range from 4.0 to 11, and is preferably within the pH range of physiological conditions from 6.8 to 7.6. If the pH during the reaction is less than 4.0, then the time required for gelation may lengthen, whereas if the pH exceeds 11, then biological samples being used may sometimes be affected.

There are no particular limitations on the temperature during the reaction, and the temperature is, for example, typically within a range from 4° C. to 70° C., and preferably within a range from 15° C. to 40° C. If the temperature during the reaction is less than 4° C., then the time required for gelation may lengthen, whereas if the temperature exceeds 70° C., then the peroxidase may sometimes be deactivated.

In terms of the reaction time, production of the hydrogel can be achieved in an extremely short time of, for example, about 30 minutes to 1 hour. If, for example, a trace amount of hydrogen peroxide (for example, about 1 mM) is also added, a similar gel can be obtained in several minutes (for example, within 10 minutes).

The reaction may be performed, for example, by mixing a solution of the polyethylene glycol having two or more thiol groups and a solution of the phenol compound, subsequently adding a solution of the peroxidase to the mixed solution, and then either leaving the resulting mixture to stand or stirring the mixture at a prescribed temperature for a prescribed period of time.

The hydrogel obtained in the method for producing a hydrogel according to an embodiment of the present invention is a structure in which the polyethylene glycol having two or more thiol groups has undergone crosslinking via disulfide bonds. The gel fraction of the obtained hydrogel (the weight proportion of the polymer used in the gel formation that participates in hydrogel formation) is, for example, within a range from 80 to 96%.

Further, the storage modulus (G') of the obtained hydrogel is, for example, about 1,000 to 100,000 Pa, and the equilibrium swelling ratio ($Q_M$) is, for example, about 30 to 45%.

In the method for producing a hydrogel according to the present embodiment, the polyethylene glycol having two or more thiol groups and a thiol compound having one or more thiol groups may be crosslinked using a peroxidase in the presence of a phenol compound. This enables a thiol compound having at least one function among cell adhesion, differentiation induction, proliferation promotion, biodegradability, specific affinity for biological molecules, electrical charging (electrostatic interaction function) and hydrophobicity to be incorporated within the gel network, thereby enabling the production of a functional hydrogel.

There are no particular limitations on the thiol compound having one or more thiol groups, and examples include functional peptides such as cell adhesion peptides having a cysteine residue, natural biopolymers such as K-casein having one or more thiol groups, and natural polymers such as gelatin, hyaluronic acid and heparin which have been chemically modified with one or more thiol groups. For example, by crosslinking the polyethylene glycol having two or more thiol groups and a cell adhesion peptide having a cysteine residue using a peroxidase in the presence of a phenol compound, the physiologically inactive PEG hydrogel is imparted with cell adhesion properties, meaning a cell-adhesive hydrogel can be obtained.

In the method for producing a hydrogel according to the present embodiment, the polyethylene glycol having two or more thiol groups and a phenol compound having one or more thiol groups may be crosslinked using a peroxidase. This enables a phenol compound having one or more thiol groups and having at least one function among cell adhesion, differentiation induction, proliferation promotion, biodegradability, specific affinity for biological molecules, electrical charging (electrostatic interaction function) and hydrophobicity to be incorporated within the gel network, thereby enabling the production of a functional hydrogel. In this case, it is thought that the phenol compound having one or more thiol groups promotes coupling between thiol groups as a phenol compound. By emulsifying this type of functional hydrogel in a solution, for example by adding a surfactant, and then performing an ultrasonic treatment or the like, a nanogel having, for example, a particle size of about 200 nm to 5 μm can be produced. Further, this type of functional hydrogel can also be used as a carrier or the like for a drug delivery system (DDS).

There are no particular limitations on the phenol compound having one or more thiol groups, and examples include proteins such as streptavidin having both tyrosine and cysteine within the molecule. This enables the molecule to be incorporated spontaneously within the gel network, while retaining the role of a phenol compound. In this case, the phenol compound may not correspond with the low-molecular weight phenol compound having a molecular weight of not more than 500 described above.

A method for enveloping an envelopment target according to an embodiment of the present invention is a method which involves producing a hydrogel by crosslinking a polyethylene glycol having two or more thiol groups using a peroxidase in the presence of a phenol compound, and enveloping the envelopment target in the hydrogel.

For example, by mixing a solution of the polyethylene glycol having two or more thiol groups, a solution of the phenol compound, and a solution or a suspension of the envelopment target, subsequently adding a solution of the peroxidase to the mixed solution, and then either leaving the resulting mixture to stand or stirring the mixture at a prescribed temperature for a prescribed period of time, the envelopment target can be enveloped in the hydrogel under mild conditions including a low peroxidase concentration and physiological conditions, even without the addition of hydrogen peroxide. Moreover, the envelopment can be achieved in a comparatively short period of time.

In order to enable satisfactory envelopment of the envelopment target, the amount of the hydrogel relative to the envelopment target is typically set so that a hydrogel is produced in which the polymer concentration is within a range from 1 to 30 wt % relative to the solution or suspension of the envelopment target.

Further, a method for releasing an envelopment target according to an embodiment of the present invention is a method for releasing an envelopment target, which has been enveloped in a hydrogel by producing a hydrogel by crosslinking a polyethylene glycol having two or more thiol groups using a peroxidase in the presence of a phenol compound and in the presence of the envelopment target, by dissolving the hydrogel using a reducing agent.

For example, by performing envelopment within the hydrogel in the manner described above, subsequently adding a reducing agent to the system, and then either leaving the resulting mixture to stand or stirring the mixture at a prescribed temperature for a prescribed period of time, the hydrogel can be dissolved and the envelopment target released from the hydrogel by a simple method.

There are no particular limitations on the reducing agent, provided it is capable of reducing the disulfide bonds that represent the crosslinking points of the hydrogel, and examples include reducing agents such as dithiothreitol (DTT), cysteine, reduced glutathione, NADH, NADPH, TCEP (tris(2-carboxyethyl)phosphine), 2-mercaptoethanol, and sodium borohydride. Among these, from the viewpoint of biocompatibility and the like, a reducing agent derived from a natural substance such as cysteine is preferred.

The amount used of the reducing agent may be set, for example, within a range from 1 to 30 equivalents relative to the amount of disulfides (S—S bonds) within the gel.

Although there are no particular limitations on the temperature during the reduction, provided the temperature has no effect on the enveloped material, the temperature is, for example, within a range from 4° C. to 70° C., and is preferably within a range from 20° C. to 40° C.

The method for enveloping and the method for releasing the envelopment target according to these embodiments proceed under extremely mild conditions for the envelopment target such as cells, and therefore these methods are considered suitable for the production of three-dimensional scaffold materials for cells and carriers for cell transport, and also for the production of carriers for drug transport or the like.

There are no particular limitations on the envelopment target, and examples include cells, proteins, nucleic acids, sugars, drugs, synthetic polymers, nanocarbon materials, and metal nanoparticles.

EXAMPLES

The present invention is described below in further detail using a series of examples and comparative examples, but the present invention is in no way limited by the following examples.

Example 1-1

[Production of Hydrogel by HRP-Catalyzed Reaction]
(Test Method)

A 4-arm PEG-SH (weight-average molecular weight: 20,000, SUNBRIGHT (a registered trademark) PTE-200SH, manufactured by NOF Corporation) as a polyethylene glycol having two or more thiol groups, and tyramine hydrochloride as a phenol compound were each dissolved in phosphate buffered saline (PBS, pH 7.4). The thus obtained 4-arm PEG-SH aqueous solution (150 μL, 10% (w/v)) and the phenol compound aqueous solution (75 μL, 20 mM) were mixed, an HRP aqueous solution (75 μL, 20 units/mL) was then added, and the resulting mixture was left to stand at 22° C. The final concentrations of the 4-arm PEG-SH, the phenol compound and the HRP were 5% (w/v), 5 mM and 5 units/mL respectively.

Comparative Example 1

In order to evaluate the effect of the phenol compound, a test was performed in the same manner as Example 1-1 with the exception of not adding the phenol compound (tyramine hydrochloride).
(Results)

Figure 2:
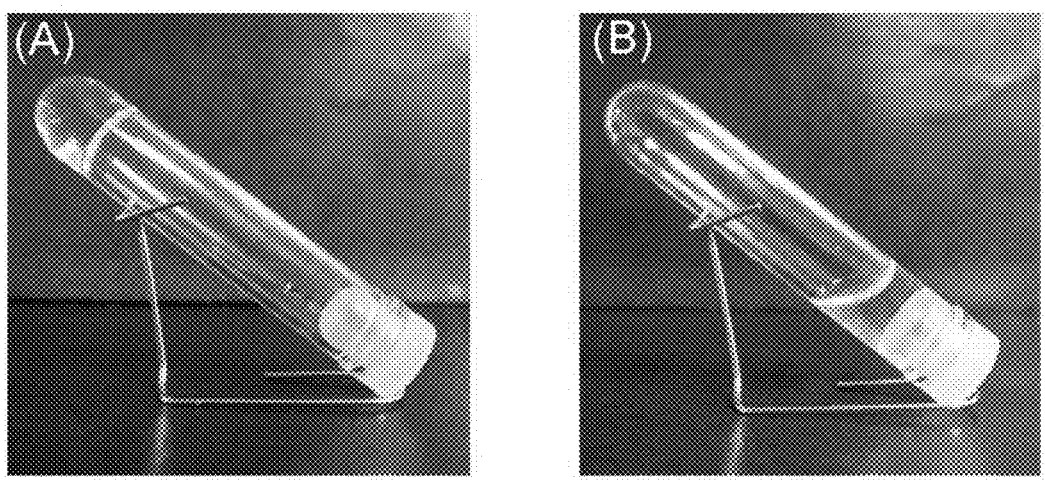
FIG. 2 shows photographs of mixed solutions (pH 7.4) of a 4-arm PEG-SH and HRP, (A) in the presence of tyramine hydrochloride (Example 1-1), and (B) in the absence of tyramine hydrochloride (Comparative Example 1).

Under the conditions of Example 1-1 in which the 4-arm PEG-SH, tyramine hydrochloride and HRP were added, gel formation was confirmed after 30 minutes (FIG. 2(A)), but under the conditions of Comparative Example 1 in which no tyramine hydrochloride was added, no gel formation was observed even after one week (FIG. 2(B)).

Figure 1:
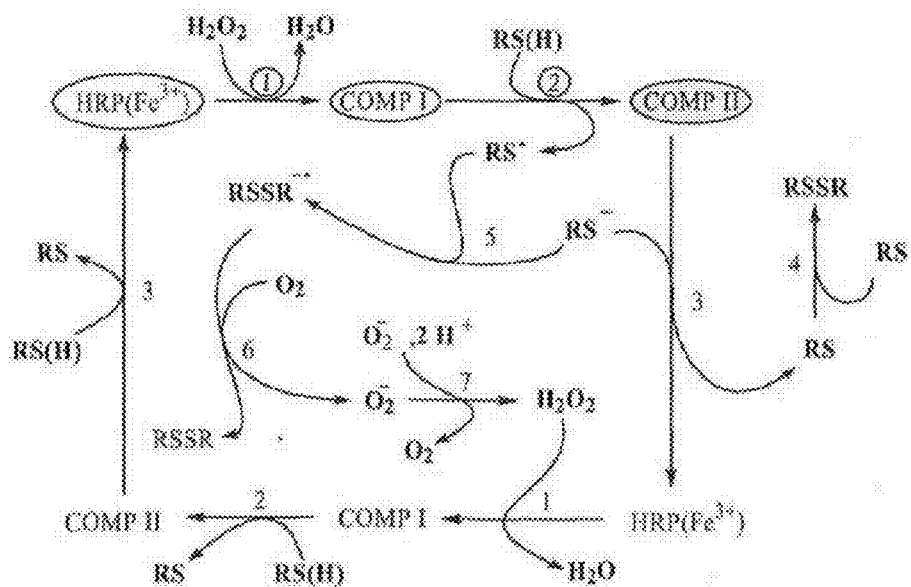
FIG. 1 is a diagram illustrating the catalytic cycle when HRP oxidizes SH (cited from Non-Patent Document 4).

In Example 1-1, compared with the method of Non-Patent Document 3, a gel was able to be produced under conditions of extremely low HRP concentration (approximately 1/300). Moreover, the gel was able to be produced under physiological conditions of pH 7.4. In Non-Patent Document 3, it is reported that gelation of the polymer aqueous solution does not proceed under conditions of pH 7.4. It is thought that this is because in the initial stage of the gelation process, the deprotonation required for SH self-oxidation proceeds very poorly. As a result, it is thought that the hydrogen peroxide required for activating the HRP is not produced efficiently, meaning the gelation of the aqueous solution does not proceed. Further, as mentioned above, it could also be said that the fact that the rate constant for the direct oxidation reaction of SH by HRP (COMP (II)) (reaction 3 in FIG. 1) is extremely low is another contributing factor. Even in Example 1-1, almost no self-oxidation of SH occurs, and therefore the concentration of hydrogen peroxide in the system in the initial stage is predicted to be extremely low, but it is thought that by adding the phenol compound to the system, the efficiency of the HRP catalytic cycle is increased, coupling between thiol groups is promoted, and the production of hydrogen peroxide within the catalytic cycle proceeds more efficiently, meaning gel formation proceeds with a low concentration of HRP and under physiological conditions of pH 7.4, even without adding hydrogen peroxide.

Figure 3:
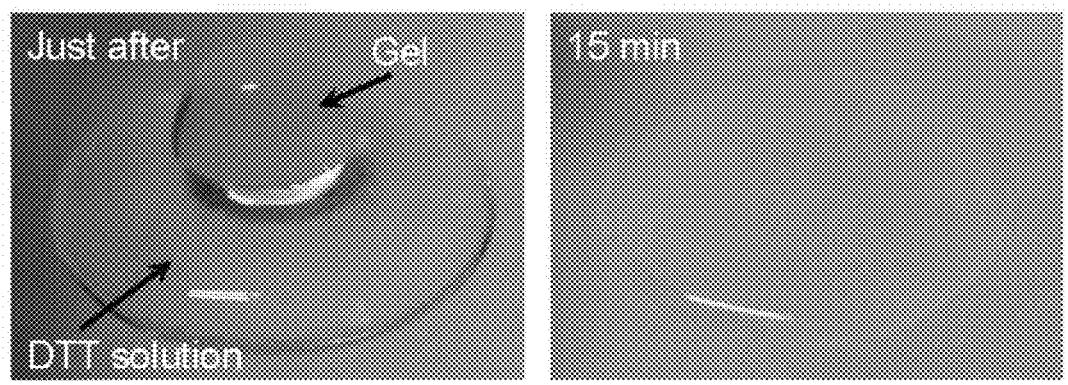
FIG. 3 shows photographs of the state of a hydrogel produced in Example 1-1, just after immersion in an aqueous solution of dithiothreitol (DTT) (left side), and 15 minutes after immersion (right side).

Further, as a result of reducing the produced hydrogel using a dithiothreitol (DTT) aqueous solution (50 mM, 1 mL), dissolution was observed in about 15 minutes (see FIG. 3), indicating that the crosslinking between polymer molecules was due to disulfide bonds.

Examples 1-2 to 1-7

With the exception of using phenol (Example 1-2), Gly-Tyr (Example 1-3), hydroquinone (Example 1-4), resorcinol (Example 1-5), catechol (Example 1-6) and serotonin (Example 1-7) respectively as the phenol compound instead of tyramine hydrochloride, tests were performed in the same manner as Example 1-1.

Figure 4:
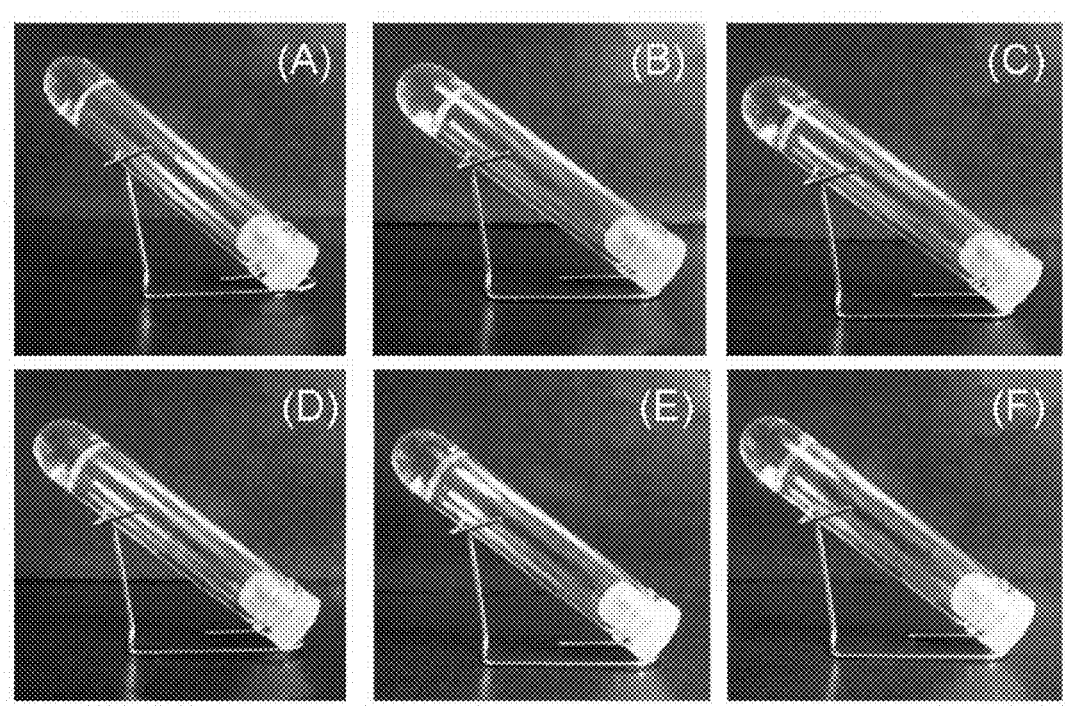
FIG. 4 shows photographs of mixed solutions (pH 7.4) of a 4-arm PEG-SH and HRP when (A) phenol (Example 1-2), (B) Gly-Tyr (Example 1-3), (C) hydroquinone (Example 1-4), (D) resorcinol (Example 1-5), (E) catechol (Example 1-6), and (F) serotonin (Example 1-7) are used as the phenol compound.

Gel formation was observed in a similar manner for these other phenol compounds (see FIG. 4).

Example 2

Figure 5:
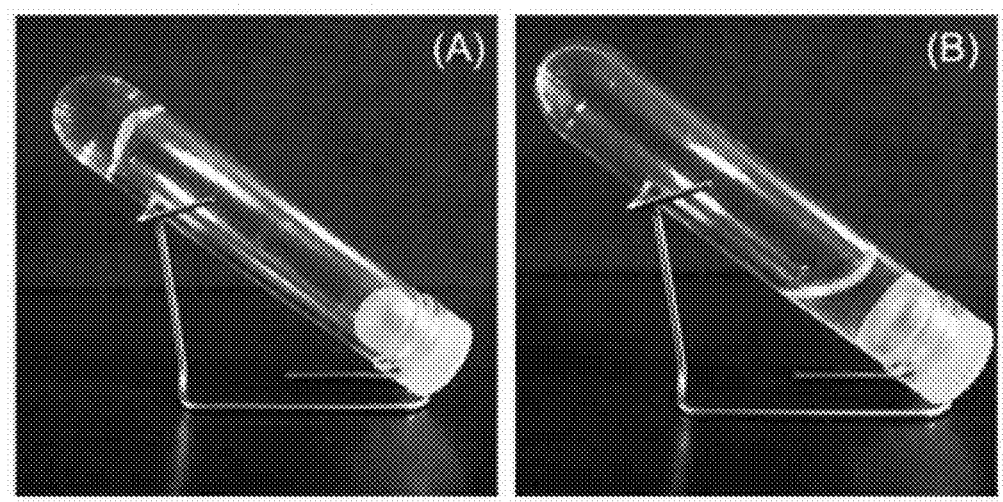
FIG. 5 shows photographs from Example 2 of mixed solutions (pH 7.4) of a 4-arm PEG-SH, HRP and tyramine hydrochloride, (A) in the absence of a catalase, and (B) in the presence of a catalase.

[Effects of Catalase]
In this test, catalase which decomposes hydrogen peroxide into oxygen and water was added to the system, and the effect on the gelation of the polymer aqueous solution was investigated. It was predicted that if hydrogen peroxide generated within the system was participating in the gelation, then the addition of catalase should lengthen the gelation time. In this investigation, tyramine hydrochloride was used as the phenol compound.
(Test Method)
The 4-arm PEG-SH and tyramine hydrochloride were each dissolved in PBS (pH 7.4). The thus obtained 4-arm PEG-SH aqueous solution (100 µL, 15% (w/v)) and the tyramine aqueous solution (100 µL, 15 mM) were mixed, and an HRP aqueous solution (50 µL, 30 units/mL) was then added. Finally, a catalase aqueous solution (50 µL, 0.27 mg/mL) was added, and the resulting mixture was left to stand at 22° C. The final concentrations of the 4-arm PEG-SH, the tyramine hydrochloride, the HRP and the catalase were 5% (w/v), 5 mM, 5 units/mL and 4.5×10$^{-2}$ mg/mL respectively. In a similar manner, a test was also performed under conditions in which no catalase was added.
(Results)
FIG. 5 shows photographs one hour after gel production. Under the conditions in which no catalase was added, gel formation was confirmed after about 40 minutes (FIG. 5(A)), but under the conditions in which catalase was added, gelation of the polymer aqueous solution was inhibited (FIG. 5(B)). Based on these results, it was evident that hydrogen peroxide was being generated within the system, and that the generated hydrogen peroxide was participating in the gelation of the polymer aqueous solution.

Example 3

[Investigation of Gelation Time (Phenol Compound)]
The effect of the phenol compound used on the gelation time of the polymer aqueous solution was investigated.
(Test Method)
The 4-arm PEG-SH and the phenol compound were each dissolved in PBS (pH 7.4). Next, 100 µL of the thus obtained PEG-SH aqueous solution (10% (w/v)) and 50 µL of the phenol compound aqueous solution (20 mM) were placed in a 48-well plate dish and stirred (stirrer: length 10: mm, width: 3 mm, stirring rate: 200 rpm). Subsequently, 50 µL of an HRP aqueous solution (20 units/mL) was added to each well, and the time taken for gelation was measured. At this point, the final concentrations of the 4-arm PEG-SH, the phenol compound and the HRP were 5% (w/v), 5 mM and 5 units/mL respectively. Further, using tyramine hydrochloride as the phenol compound, the final concentration of the tyramine hydrochloride was altered to 0.5, 1, 5, 10, 50 or 100 mM, and the effect of the tyramine concentration on the gelation time was investigated. Moreover, the final concentration of HRP was altered to 5, 10 or 50 units/mL, and the effect of the HRP concentration on the gelation time was investigated in a similar manner.

In these tests, the time when the liquid surface of the mixed solution rose and lost fluidity was adjudged to indicate gelation.
(Results)
The gelation times for the polymer aqueous solution evaluated using the various phenol compounds are shown in Table 1. The gelation time under various conditions was fastest with tyramine, at about 30 minutes, whereas 12 hours or longer were required with catechol. This means that the variety of phenol compound has a large effect on the gelation time. The reason for this observation is not clear at this stage, but it is thought that HRP substrate recognition and the stability of the produced phenoxy radicals may be contributing factors.

TABLE 1

Effect of various phenol compounds on gelation time
(mean ± standard deviation for n = 3)

| Phenol compound | Gelation time [h] |
| --- | --- |
| tyramine hydrochloride | 0.50 ± 0.02 |
| phenol | 0.66 ± 0.07 |
| Gly-Tyr | 0.67 ± 0.08 |
| resorcinol | 1.1 ± 0.05 |
| hydroquinone | 1.4 ± 0.04 |
| serotonin | 8.7 ± 0.11 |
| catechol | >12 |

Figure 6:
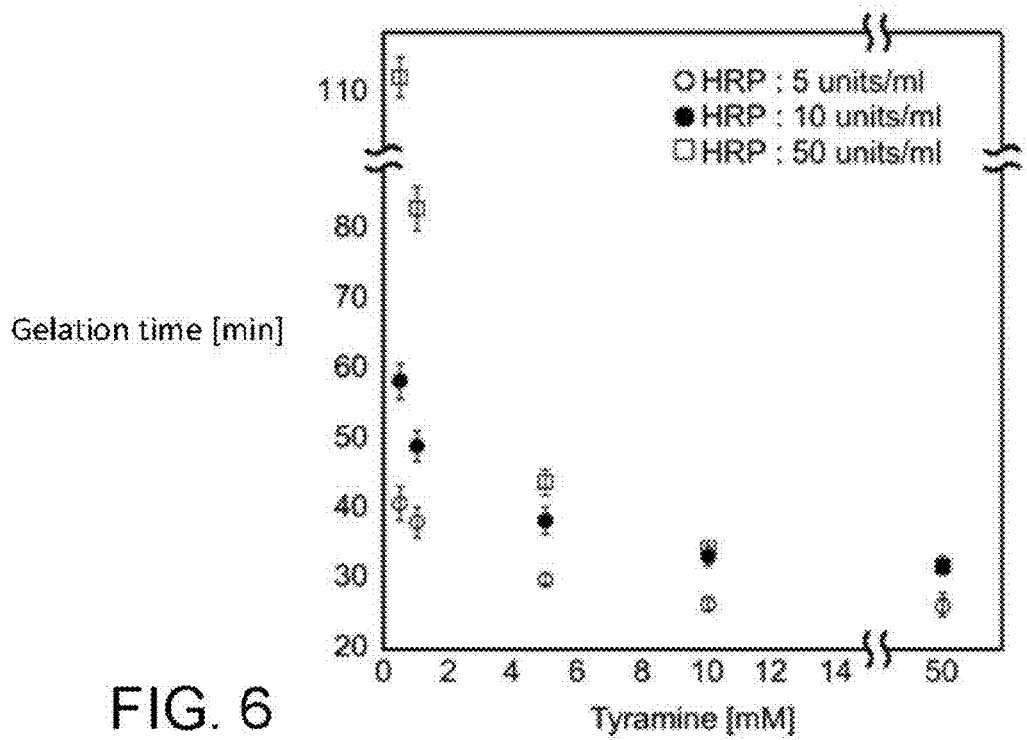
FIG. 6 is a diagram illustrating the effect of the HRP concentration and the tyramine hydrochloride concentration on the gelation time in Example 3.

Next, the effect of the concentration of each component on the gelation time was investigated. The gelation time for the polymer aqueous solution showed a tendency to increase with increasing HRP concentration (see FIG. 6). It is thought that this is because formation of dityramine in the system inhibits the radical rearrangement reaction from the phenoxy radical to the thiol radical. It is thought that by increasing the HRP concentration, the production rate for phenol radicals increases, resulting in an acceleration in the formation of dityramine. In terms of the tyramine concentration, the gelation time showed a tendency to shorten with increasing tyramine concentration (see FIG. 6). It is thought that this is due to an increase in the production rate for phenol radicals in the system.

Moreover, gelation times were also measured under high tyramine concentration conditions of 100 and 200 mM (the concentrations of the other components were set to PEG-SH: 5% (w/v) and HRP: 5 units/mL). The results revealed an increasing tendency with gelation times of 27.1±1.2 min and 34.8±1.1 min respectively. It is thought that, as described above, this increase was the result of inhibition of the radical rearrangement reaction due to the formation of dityramine in the system.

Further, based on the fact that the shortest gelation time in the results of Non-Patent Document 3 was about 110 min, it was evident that using the gelation process of the present invention succeeded in shortening the gelation time about 4-fold. Furthermore, the HRP concentration in the system of the present invention was extremely low compared with that of the Non-Patent Document 3 (about 1/300), indicating a hydrogel production method with excellent redox responsiveness.

Example 4

[Investigation of Gelation Time (Polyethylene Glycol)]

The effect of the concentration of the polyethylene glycol having two or more thiol groups on the gelation time was investigated.

(Test Method)

The 4-arm PEG-SH and tyramine hydrochloride were each dissolved in PBS (pH 7.4). Next, 100 μL of the thus obtained PEG-SH aqueous solution (10% (w/v)) and 50 μL of the tyramine hydrochloride aqueous solution (20 mM) were placed in a 48-well plate dish and stirred (stirrer: length 10: mm, width: 3 mm, stirring rate: 200 rpm). Subsequently, 50 μL of an HRP aqueous solution (20 units/mL) was added to each well, and the time taken for gelation was measured. At this point, the final concentrations of the 4-arm PEG-SH, the tyramine hydrochloride and the HRP were 5, 10 or 15% (w/v), 5 mM and 5 units/mL respectively.

In these tests, the time when the liquid surface of the mixed solution rose and lost fluidity was adjudged to indicate gelation.

(Results)

The gelation times evaluated using various 4-arm PEG-SH concentrations are shown in Table 2. The gelation time for the polymer aqueous solution was independent of the 4-arm PEG-SH concentration, and substantially similar values were obtained (about 30 min). These results indicated that it is not the reaction between polymer molecules, but rather the reaction leading to the formation of the thiol radicals that is rate limiting.

TABLE 2

Effect of 4-arm PEG-SH concentration on gelation time (mean ± standard deviation for n = 3)

| 4-arm PEG-SH concentration [% (w/v)] | Gelation time [min] |
| --- | --- |
| 5 | 30.1 ± 0.9 |
| 10 | 30.0 ± 1.7 |
| 15 | 30.6 ± 2.0 |

Example 5

[Dissolution of Hydrogel Using Reducing Agent]

Because the crosslinking points in the PEG-SH hydrogels produced in the examples are disulfide bonds, the hydrogels can be dissolved easily by reduction. Accordingly, in this investigation, the dissolution behavior of the gel was investigated using a reducing agent. Cysteine, which is thought to enable the dissolution of the gel to proceed under mild conditions, was used as the reducing agent in the evaluation. Further, tyramine hydrochloride was used for the phenol compound.

(Test Method)

The 4-arm PEG-SH and tyramine hydrochloride were each dissolved in PBS (pH 7.4). The thus obtained 4-arm PEG-SH aqueous solution (150 μL, 10% (w/v)) and the tyramine aqueous solution (75 μL, 20 mM) were mixed, the resulting mixture was then placed in a mold, an HRP aqueous solution (75 μL, 20 units/mL) was subsequently added, and the resulting mixture was left to stand at room temperature (22° C.) for 1 hour, thus producing a disc-shaped PEG-SH hydrogel (diameter: about 15 mm, thickness: about 2 mm). The final concentrations of the 4-arm PEG-SH, the HRP and the tyramine hydrochloride were 5% (w/v), 5 units/mL and 5 mM respectively. The thus produced hydrogel was immersed in a 0, 1, 5 or 10 mM cysteine solution (in PBS) (5 mL) and incubated at 37° C., and the change in weight of the gel over time was evaluated. For those samples that had not dissolved one hour after starting testing, the cysteine solution was replaced with a fresh cysteine solution that was added to the undissolved sample, and the investigation was continued.

(Results)

Figure 7:
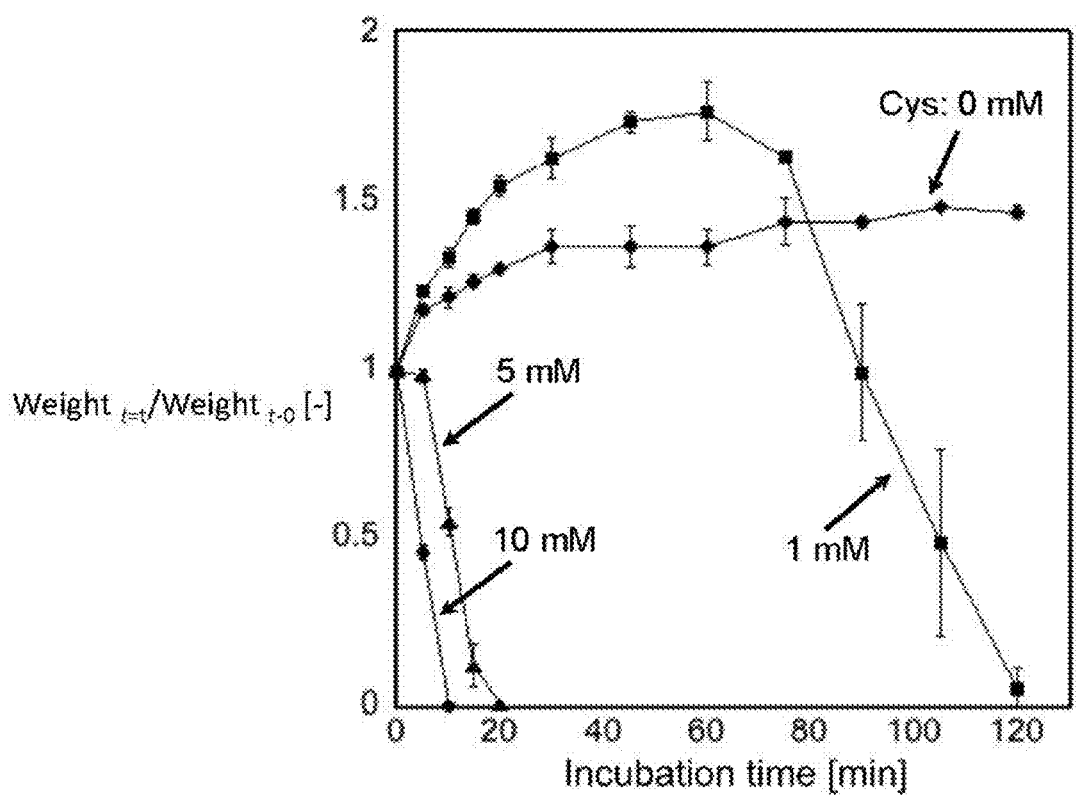
FIG. 7 is a diagram illustrating the change in weight over time of a PEG-SH hydrogel immersed in 0, 1, 5 and 10 mM cysteine solutions (in PBS) in Example 5.

The change in weight of the hydrogel over time under the various conditions is shown in FIG. 7. Only the hydrogel immersed in the cysteine solutions dissolved, whereas no dissolution was observed for the hydrogel immersed in PBS. These results indicated that the gel could be dissolved by using cysteine as a reducing agent. Further, the increase in gel weight under conditions of immersion in PBS was thought to be due to swelling. In terms of the effect of the cysteine concentration, a higher concentration tended to result in a shortened dissolution time, and it was evident that at concentrations of 5 mM or higher, extremely rapid gel dissolution within 30 minutes was possible.

Example 6

[Cell Envelopment Test and Release Test]

In conventional gel production methods using an HRP-catalyzed reaction, hydrogen peroxide must be added directly to the system, but in the gel production method of the present examples, the hydrogen peroxide substrate is produced gradually within the system and is then rapidly consumed by the HRP, resulting in an extremely mild gel production method that is thought to be particularly suited to production methods for cell-enveloping carriers. Accordingly, in this investigation, cell envelopment tests within PEG-SH hydrogels were performed, and the effect of the gelation process on the cell viability was evaluated. Moreover, in the investigation described above, it was evident that using the amino acid cysteine enabled ready dissolution of the gel, and therefore an enveloped cell release test was also performed.

(Test Method)

Cell Envelopment Test

The 4-arm PEG-SH and tyramine hydrochloride were each dissolved in PBS (pH 7.4). The thus obtained 4-arm PEG-SH aqueous solution (250 µL, 10% (w/v)), the tyramine aqueous solution (100 µL, 25 mM), and an L929 fibroblast suspension (in MEM (10% FBS)) (100 µL, $2\times10^6$ cells/mL) were mixed, an HRP aqueous solution (50 µL, 50 units/mL) was subsequently added, and the resulting mixture was then added to a 6-well plate dish (500 µL) and left to stand in an incubator for one hour to produce a gel. The final concentrations of the 4-arm PEG-SH, the tyramine hydrochloride and the HRP were 5% (w/v), 5 mM and 5 units/mL respectively. Further, the number of inoculated cells was adjusted to $2\times10^5$ cells/well. Following gelation, 5 mL of a medium was added, and the mixture was left to stand in an incubator, with 2 mL of fresh medium being substituted after one hour and then after 5 hours. After 3 hours and then after 24 hours, the gel was washed (5 times) with PBS (5 mL), a Cellstain-DoubleStaining Kit was used to classify viable cells and dead cells by staining (wherein green indicates a viable cell and red indicates a dead cell), the sample was inspected using a fluorescence microscope, and the viability was calculated from the number of viable cells and the number of dead cells.

Release Test

Cell envelopment within a gel was performed in accordance with the operations described above, and the gel was cultured for 24 hours. Subsequently, the gel was washed (5 times) with PBS (5 mL), 5 mL of a cysteine solution (5 mM) was added to each well, and the resulting mixture was left to stand for 30 minutes inside an incubator. After 30 minutes, following confirmation that the gel had dissolved, the cells were collected and inoculated into a 24-well dish. Four hours after inoculation and then 48 hours after inoculation, the cells were inspected under a microscope.

(Results)

Figure 8:
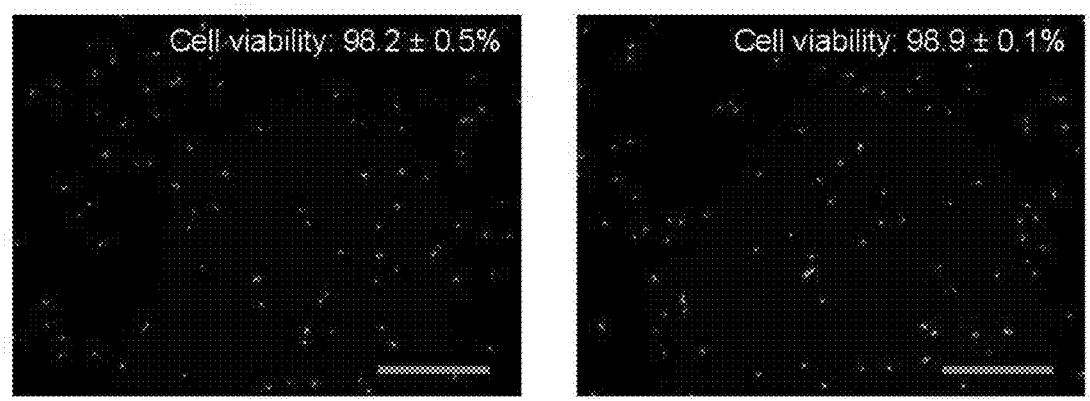
FIG. 8 shows microscope photographs from Example 6 of L929 fibroblasts enveloped in a PEG-SH hydrogel, 3 hours after envelopment (left side), and 24 hours after envelopment (right side).
Figure 9:
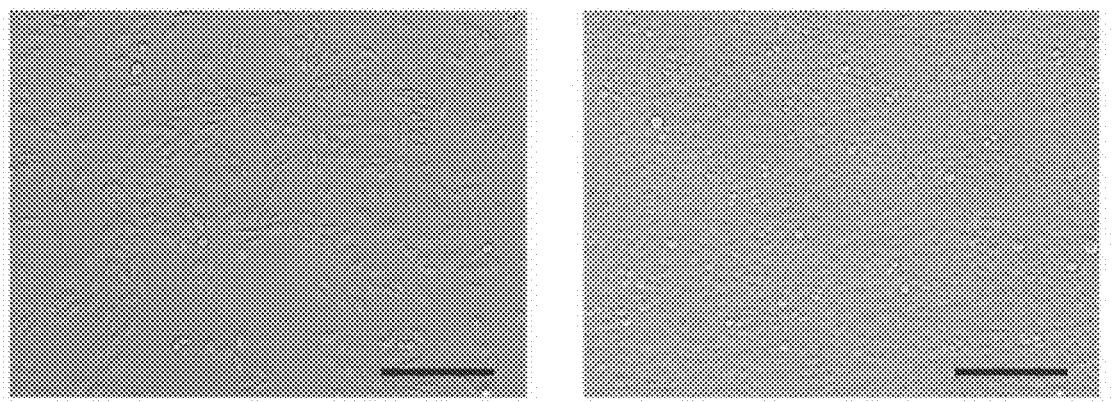
FIG. 9 shows microscope photographs from Example 6 of L929 fibroblasts, 4 hours after inoculation on a cell culture (left side), and 48 hours after inoculation (right side).

In the gel production method of the present examples, it is thought that because the hydrogen peroxide produced within the system is rapidly consumed by the HRP, the crosslinking reaction between polymer molecules proceeds under extremely mild conditions. Accordingly, it is thought that the gel production method of these examples is extremely suited to the production of three-dimensional scaffold materials for cells, and carriers for cell immobilization. Hence, a cell envelopment test into a PEG-SH hydrogel was attempted. The enveloped cells maintained a high viability after 3 hours culturing (viability: 98.2±0.5%, see left side of FIG. 8). Further, it was evident that the cell viability had also undergone almost no reduction after 24 hours (viability: 98.9±0.1%, see right side of FIG. 8). Next, collection of the enveloped cells that had been cultured for 24 hours was attempted. A 5 mM cysteine solution was added to each well, and after incubation for 30 minutes, the supernatant solution was collected, and following a centrifugation operation, the cells were reinoculated into a 24-well plate. After 4 hours, adhesion of the inoculated cells to the dish, and spreading of the cells was observed (see left side of FIG. 9). Based on the fact that almost no free cells (dead cells) were observed in the supernatant medium at this time, and the fact that cell proliferation was observed after 48 hours incubation (see right side of FIG. 9), it was evident that the gelation process of the polymer aqueous solution and the gel dissolution operation using a cysteine solution were very mild in relation to the viability of the cells. The above results indicated success in enveloping the cells within the gel and then releasing the cells from the gel while maintaining high cell viability.

Example 7

[Evaluation of Hydrogel Physical Properties]

(Test Method)

Measurement of Rheology

The final concentration of the 4-arm PEG-SH was changed to 5, 10 or 15% (w/v), and the storage modulus (G') was measured using a rheometer (manufactured by Anton Paar GmbH). During these measurements, evaluations were performed while the frequency was changed from 0.1 to 10 Hz. Further, the final concentrations of the tyramine hydrochloride and the HRP were set to 5 mM and 5 units/mL respectively.

Evaluation of Equilibrium Swelling Ratio ($Q_M$) and Gel Content

The 4-arm PEG-SH, tyramine hydrochloride and HRP were each dissolved in PBS (pH 7.4). Next, 150 µL of the 4-arm PEG-SH aqueous solution, 75 µL of the tyramine aqueous solution and 75 µL of the HRP aqueous solution were mixed, and the resulting mixture was placed in a mold. The final concentrations of the 4-arm PEG-SH, the HRP and the tyramine hydrochloride were 5, 10 or 15% (w/v), 5 units/mL and 5 mM respectively. After 4 hours, each of the produced disc-shaped 4-arm PEG-SH hydrogels (diameter: about 15 mm, thickness: about 2 mm) was immersed in 10 mL of PBS for 3 days in an environment at 37° C., and the weight of the hydrogel after swelling ($M_S$) was measured. Subsequently, the hydrogel was subjected to freeze drying, the dry weight of the hydrogel ($M_D$) was measured, and the equilibrium swelling ratio ($Q_M=M_S/M_D$) was calculated.

Further, 15, 30 and 45 mg ($W_p$) samples of the 4-arm PEG-SH were dissolved in PBS (pH 7.4), and disc-shaped 4-arm PEG-SH hydrogels were produced (diameter: about 15 mm, thickness: about 2 mm). The final concentrations of the 4-arm PEG-SH, the HRP and the tyramine hydrochloride were 5, 10 and 15% (w/v), 5 units/mL and 5 mM respectively. Each of the produced gels was immersed in 10 mL of Milli-Q water for 3 days in an environment at 37° C., and salts and non-crosslinked 4-arm PEG-SH were removed. Subsequently, the hydrogel was dried, the dry weight ($W_D$) of the hydrogel was measured, and the gel content ($=W_D/W_p \times 100$) was calculated.

(Results)

Figure 10:
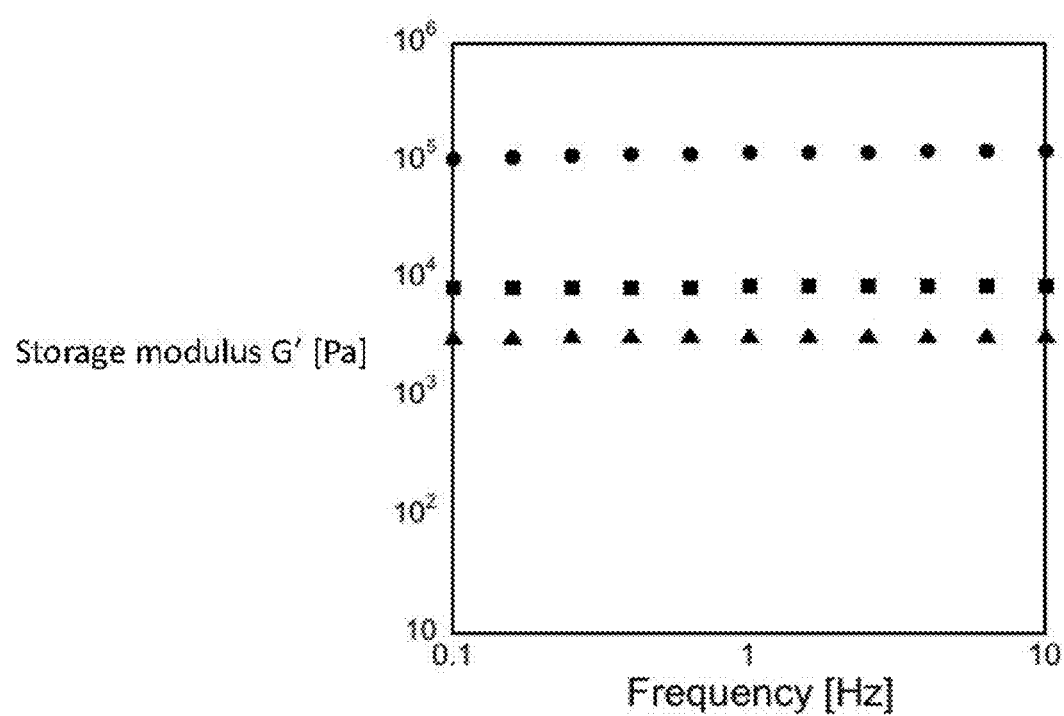
FIG. 10 is a diagram illustrating the hydrogel storage modulus (G') relative to the concentration of a 4-arm PEG-SH in Example 7 (black circle: 15 wt %, black square: 10 wt %, black triangle: 5 wt %).

The physical properties of hydrogels obtained with various 4-arm PEG-SH concentrations were evaluated. The gel storage modulus (G') displayed a tendency to increase with increases in the polymer concentration (see FIG. 10). In contrast, the equilibrium swelling ratio ($Q_M$) of the gel displayed a tendency to decrease with increases in the polymer concentration (see Table 3). It is thought that the gel crosslinking density is involved in these results. In other words, it is thought that the above results are due to the crosslinking density increasing as the polymer concentration increases. Further, in terms of the gel content, the content was maintained at a value of at least 80% under all of the conditions (see Table 3).

TABLE 3

Effect of 4-arm PEG-SH concentration on equilibrium swelling ratio $Q_M$ and gel content (mean ± standard deviation for n = 3)

| 4-armPEG-SH concentration [% (w/v)] | Equilibrium swelling ratio $Q_M$ [—] | Gel content [%] |
| --- | --- | --- |
| 5 | 42.5 ± 0.4 | 85.4 ± 5.1 |
| 10 | 34.4 ± 0.7 | 83.5 ± 3.6 |
| 15 | 29.7 ± 0.7 | 81.1 ± 2.5 |

Example 8

[Evaluation of Gel Content of 4-Arm PEG-SH Hydrogel Produced at Low Tyramine Concentration (and Various HRP Concentrations)]
(Test Method)

A 15 mg ($W_p$) sample of the 4-arm PEG-SH was dissolved in PBS (pH 7.4), and a disc-shaped 4-arm PEG-SH hydrogel was produced (diameter: about 15 mm, thickness: about 2 mm). At this point, the final concentrations of the 4-arm PEG-SH, the HRP and the tyramine hydrochloride were 5% (w/v), 5 units/mL and 0.5 mM respectively. After 8 hours, the produced gel was immersed in 10 mL of Milli-Q water for 3 days in an environment at 37° C., and salts and non-crosslinked 4-arm PEG-SH were removed. Subsequently, the hydrogel was dried, the dry weight ($W_D$) of the hydrogel was measured, and the gel content (=$(W_D/W_p)$× 100) was calculated.
(Results)

The gel content of the 4-arm PEG-SH gel produced at low tyramine concentration was independent of the HRP concentration, and exhibited a gel content value of 90% under all of the conditions (see Table 4). Based on these results, it was evident that a gel having a high crosslinking density could be produced even at low tyramine concentration.

TABLE 4

Effect of HRP concentration on gel content (mean ± standard deviation for n = 3)

| HRP concentration [U/mL] | Gel content [%] |
| --- | --- |
| 50 | 91.3 ± 2.2 |
| 10 | 90.5 ± 1.2 |
| 5 | 93.0 ± 3.6 |

Example 9

[Functionalization of 4-Arm PEG-SH Gel Using Cell Adhesion Peptide]
(Test Method)

Using a peptide containing a cysteine residue (C), functionalization of the 4-arm PEG-SH gel was attempted. The 4-arm PEG-SH, tyramine hydrochloride, a cell adhesion peptide (GRGDSGGC) and HRP were each dissolved in PBS (pH 7.4). The 4-arm PEG-SH aqueous solution (50 μL, 30% (w/v)), the tyramine aqueous solution (5 μL, 150 mM) and the GRGDSGGC aqueous solution (90 μL, 16.67 mM) were mixed, the HRP aqueous solution (5 μL, 150 units/mL) was added, the resulting mixture (150 μL) was placed in a 48-well plate dish, and an RGD peptide-immobilized gel was produced. The final concentrations of the 4-arm PEG-SH, the tyramine hydrochloride, the HRP and the GRGDSGGC were 10% (w/v), 5 mM, 5 units/mL and 10 mM respectively. The thus produced gel was washed 3 times with PBS and once with an MEM medium (10% FBS). Following washing, each well was inoculated with L929 fibroblasts at a rate of 4×10⁴ cells/well, and then cultured for 24 hours. After culturing, the wells were inspected under a microscope. Further, a gel containing no added adhesion peptide was investigated in the same manner as a control.
(Results and Observations)

Figure 11:
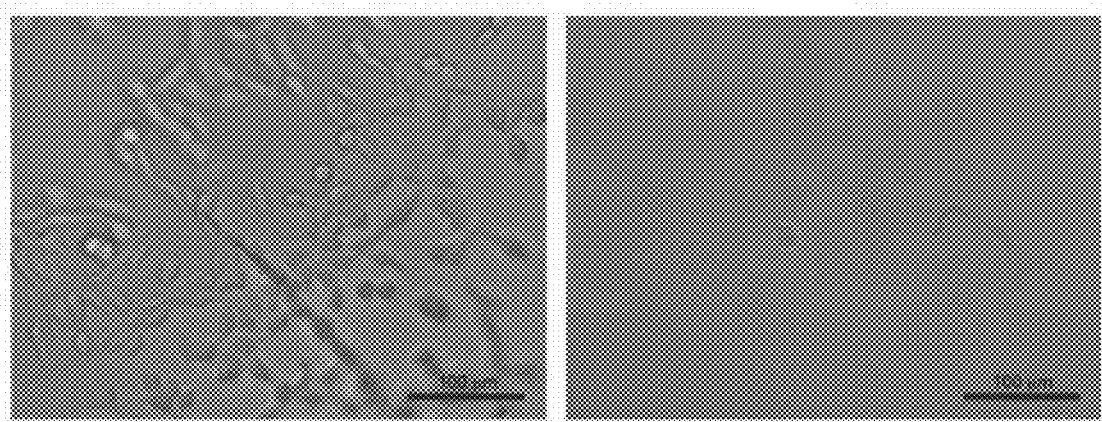
FIG. 11 shows microscope photographs from Example 9 of L929 fibroblasts 24 hours after inoculation on the surface of a 4-arm PEG-SH, in the presence of an RGD peptide (left side), and in the absence of an RGD peptide (right side).

After culturing for 24 hours, adhesion and spreading of the cells was observed on the gel containing the immobilized adhesion peptide (see left side of FIG. 11). In contrast, in the case of the gel containing no adhesion peptide, almost none of the cells had undergone adhesion, and no spreading of the cells was observed (right side of FIG. 11). Based on the above results, it was evident that using an adhesion peptide containing a cysteine residue succeeded in imparting cell adhesiveness to the physiologically inactive PEG hydrogel. Further, based on the above results it is thought that various functional hydrogels should be able to be produced by incorporating a cysteine residue not only into RGD peptides, but also into other peptides.

Example 10

[Production of Hydrogel]

An 8-arm PEG-SH (weight-average molecular weight: 20,000, SUNBRIGHT (a registered trademark) HGEO-200SH, manufactured by NOF Corporation) and tyramine hydrochloride were each dissolved in PBS (pH 7.4). Following mixing of these two aqueous solutions, an HRP aqueous solution was then added, and the resulting mixture was left to stand at 22° C. The final concentrations of the 8-arm PEG-SH, the tyramine hydrochloride and the HRP were 5% (w/v), 5 mM and 5 units/mL respectively. As a result, in a similar manner to the 4-arm PEG-SH, gel formation of the 8-arm PEG-SH was observed under conditions of added tyramine hydrochloride and HRP.

As described above, by adding a phenol compound to an HRP-SH modified polymer mixed solution, a redox-responsive hydrogel was able to be produced. Compared with conventional methods, this method is superior in terms of (1) extremely low HRP concentration conditions, (2) the ability to produce a gel under physiological conditions (pH 7.4), and (3) a comparatively rapid gelation time. Further, by using a cysteine solution, the produced hydrogel was able to be readily dissolved. Moreover, because the materials in the gelation process and the dissolution process were extremely mild in relation to the cells, it is thought that these gel production methods of the above examples are suitable for the production of three-dimensional scaffold materials for cells and carriers for cell transport. Furthermore, functional hydrogels were also able to be produced.

Example 11

[Preparation of SA Recombinant]

An expression plasmid vector (SEQ ID NO: 3) of an SA recombinant having HHHHHHC added to the N-terminal of streptavidin (SA) and GGGGY added to the C-terminal (hereafter abbreviated as C-SA-Y, SEQ ID NO: 1), and an expression plasmid vector (SEQ ID NO: 4) of an SA recombinant having only HHHHHHC added to the N-terminal of streptavidin (SA) (hereafter abbreviated as C-SA, SEQ ID NO: 2) were constructed using genetic engineering methods. Expression of each of the SA recombinants was performed using a T7 Express I$^q$ Competent E. coli (High Efficiency) (purchased from New England Biolabs Inc.). Main culturing was performed in 250 mL of LB medium (100 mg/L Amp), when $OD_{600}=1.00$ was reached, isopropyl β-D-1-thiogalactopyranoside (IPTG) was added at a final concentration of 1 mM, and following culturing for 9 hours at 37° C. and 130 rpm, the cells were collected by centrifugal separation.

The thus obtained *E. coli* pellets were dispersed in a buffer A (10 mM Tris-HCl, 100 mM NaCl, 1 mM EDTA, pH 8.0), 10 mg of lysozyme was added, and the resulting mixture was incubated at 4° C. for 30 minutes. Subsequently, ultrasonic disruption (3 min×3 repetitions) was performed, and then centrifugal separation was used to obtain a sediment containing the SA recombinant. The supernatant was discarded, the sediment was suspended in a buffer B (30 mM Tris-HCl, 2 mM EDTA, 0.1% Triton X-100, pH 8.0), and a centrifugal separation was performed again. This operation was repeated three times to wash the sediment, and then a similar technique was used to wash the sediment three times using the buffer A, finally yielding an SA recombinant inclusion body.

The inclusion body was dissolved in a 6 M guanidine hydrochloride solution (pH 1.5, 1 mM DTT), and a purification was performed by affinity chromatography using an Ni-NTA column. After purification, the solution containing the SA recombinant was added dropwise with vigorous stirring to a TBS solution (25 mM Tris-HCl, 150 mM NaCl, pH 7.5) containing 3 mM DTT to perform refolding. Following refolding, the solution was subjected to ammonium sulfate precipitation to precipitate the SA recombinant, which was then collected by centrifugal separation. The thus obtained SA recombinant precipitate was dissolved in Milli-Q water containing 3 mM DTT, and just before performing gel production, an ultrafiltration membrane was used to perform a concentration and a buffer exchange to Milli-Q water. The concentration of the SA recombinant was determined from the light absorbance at 280 nm ($\varepsilon_{280nm}=138{,}000$ $M^{-1}$ $cm^{-1}$).

[Production of SA-Immobilized Gel]

The C-SA-Y or the C-SA was mixed with horseradish-derived peroxidase (HRP) and a 4-arm PEG-SH (weight-average molecular weight: 20,000, SUNBRIGHT (a registered trademark) PTE-200MA, manufactured by NOF Corporation) under the conditions shown in Table 5, and after thorough pipetting, the resulting mixture was left to stand, and the state of gelation was observed. All reactions were performed in a 10 mM Tris-HCl buffer (pH 8.0), with the reactions proceeding at room temperature (22° C.).

TABLE 5

Preparation conditions and gelation times for SA-immobilized gels

|  | C-SA-Y | C-SA |
| --- | --- | --- |
| 4-armPEG-SH [mM] | 1.25 | 1.25 |
| HRP [U/mL] | 5 | 5 |
| SA recombinant [μM] | 100 | 100 |
| Volume [μL] | 20 | 20 |
| Gelation time [h] | 9 | >48 (no gelation observed) |

Figure 12:
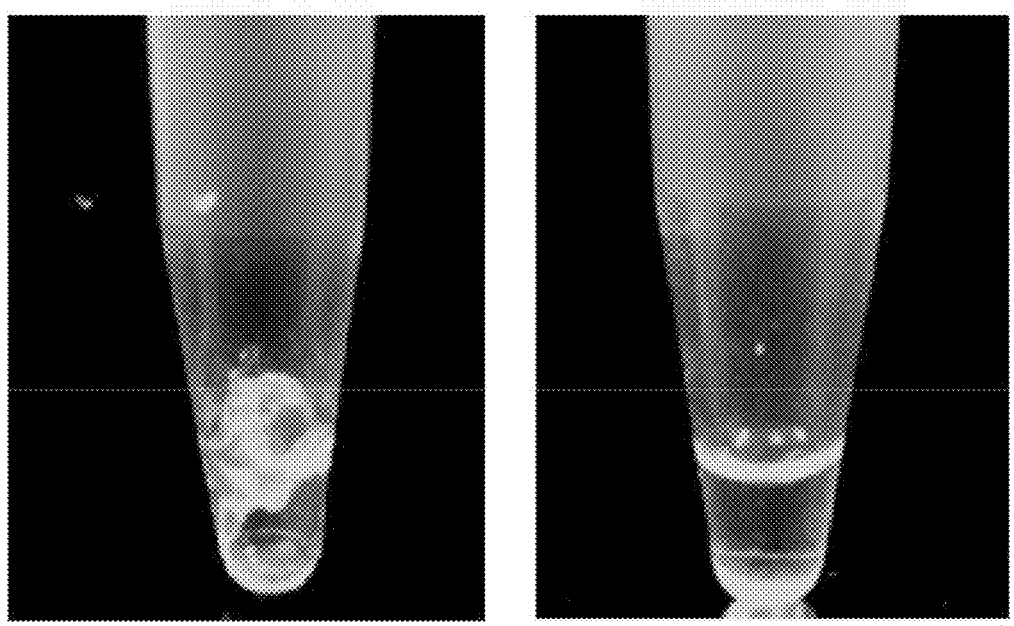
FIG. 12 shows photographs from Example 11 of mixed solutions (pH 8.0) of a 4-arm PEG-SH and HRP, under conditions including added C-SA-Y (left side), and under conditions including added C-SA (right side).

The results revealed that gelation was observed after 9 hours only under the conditions including added C-SA-Y (left side of FIG. 12). In the case of C-SA, the fact that no gelation had occurred even after 48 hours (right side of FIG. 12) indicated that the tyrosine residue introduced into the SA underwent substrate recognition by the HRP, resulting in the promotion of S—S bond formation. In this manner, production of an SA-immobilized hydrogel succeeded via a linked S—S bond formation reaction effected by tyrosine and HRP.

[Production of SA-Immobilized Nanogel]

Surfactants (Span 80: 75 mg, Tween 80: 25 mg) were added to 3.74 mL of hexane and dissolved completely.

(a) A 374 μL sample of the prepared hexane solution was used as the organic phase.

(b) 30 μL of an in-water phase (10 mM Tris-HCl, 1.25 mM 4-arm PEG-SH, 10 U/mL HRP, 100 μM C-SA-Y, pH 8.0) was prepared and added to the organic phase.

(c) Using an ultrasonic disruptor, the solution described above was subjected to an ultrasonic treatment to prepare a w/o emulsion (30 sec, duty cycle 30, output 3).

(d) A stirrer bar was added, and reaction was performed at room temperature (22° C.) for 12 hours under vigorous stirring.

(e) Alexa Fluor 647-C2-Maleimide (final concentration 30 μM) and iodoacetamide (final concentration 1 mM) were added, and after performing ultrasonic irradiation for 15 seconds, the mixture was reacted for a further 1 hour at room temperature (22° C.) under strong stirring, thereby quenching residual thiol groups and subjecting the gel to fluorescent modification.

(f) Following the addition of 150 μL of 150 mM NaCl (pH 3.0), the mixture was suspended using a Vortex. The resulting liquid was subjected to centrifugation at 10,000 rpm for 3 minutes, thereby separating the liquid into a water phase and an organic phase, and the organic phase was removed.

(g) Subsequently, 600 μL of hexane was added to the nanogel in the water phase, the hexane was suspended thoroughly using a Vortex, centrifugation at 10,000 rpm was then performed for 5 minutes, and the supernatant hexane was removed. This operation was performed twice.

(h) Subsequently, 600 μL of THF was added to the sample that had been washed with hexane, and following through suspension of the mixture using a Vortex, the mixture was separated into a THF phase and a water phase by natural settling, and the supernatant THF phase was removed. This operation was performed twice. After the second repetition, the mixture did not separate into two phases, so the nanogel was left to settle, and the supernatant THF was removed.

(i) The solution was resuspended in 150 μL of Milli-Q water, and a dialysis was performed to remove any residual THF.

(j) Alexa Fluor 488-modified biotin (0.5 equivalents relative to the SA) was added, and a reaction was performed at 4° C. for one hour. A second dialysis was then performed, and the unreacted biotin was removed.

Figure 13:
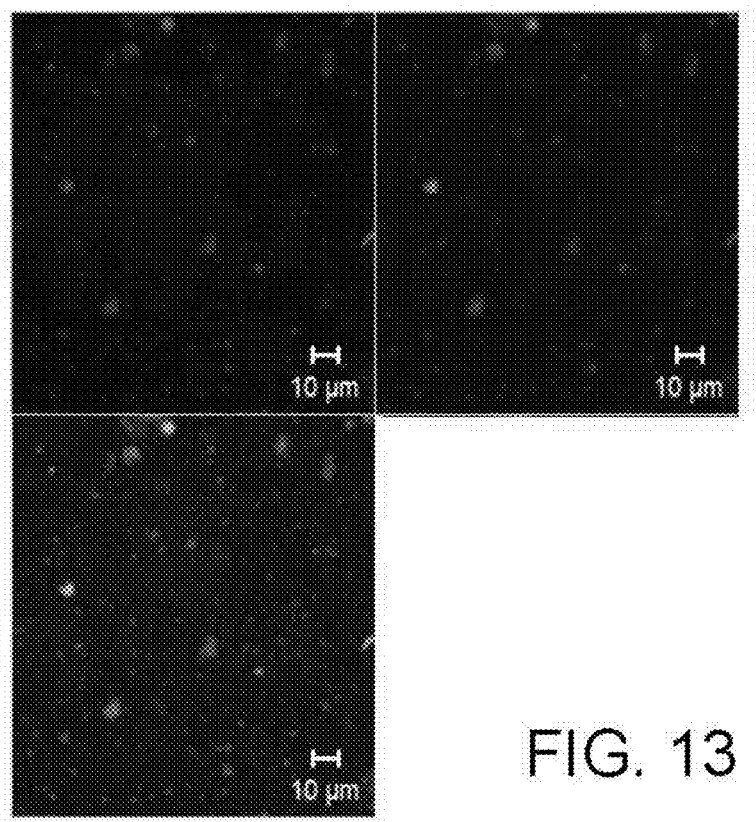
FIG. 13 shows microscope photographs of a purified nanogel viewed using a confocal microscope in Example 11.

(k) The purified nanogel was inspected using a confocal microscope (FIG. 13).

This procedure succeeded in micronizing an SA-immobilized gel using an HRP enzyme reaction, and the biotin-binding functionality of the micronized gel was confirmed.

Example 12

[Production of Functional Hydrogel Using Thiol Group-Modified Gelatin]

Gelatin is a protein obtained by partially hydrolyzing the collagen that exists within living organisms. Gelatin has an RGD motif that promotes the adhesion and proliferation of cells, and has a high level of cytocompatibility, and is therefore used as a cell culture substrate. In this example, a thiol group-modified gelatin (Gela-SH) was synthesized by modifying gelatin with thiol groups that can function as crosslinking points, and functionalization of a PEG gel was attempted by subjecting the thiol group-modified gelatin to co-crosslinking with the 4-arm PEG-SH. Further, the physical properties of the produced (PEG-SH)-(Gela-SH) hydrogel were also evaluated.

(Test Method)

[Synthesis of Thiol Group-Modified Gelatin (Gela-SH)]

First, 2.0 g of gelatin was dissolved in 100 mL of Milli-Q water, and 1.0 g of cystamine was then added. Following dissolution of the cystamine, 1.0 M HCl was used to adjust the pH of the mixed solution to 4.75. Subsequently, 0.86 g of 1-ethyl-3-(3-dimethylaminophenyl)carbodiimide hydrochloride (EDC) was added to the mixed solution and stirred at room temperature for 2 hours. During this time, in order to prevent any increase in the pH, the reaction was performed while 1.0 M HCl was used to maintain the pH at 4.75. After reacting for 2 hours, 1.0 M NaOH was used to adjust the pH of the mixed solution to 7.0. Then, 8.5 g of dithiothreitol (DTT) was added to the mixed solution as a reducing agent, 1.0 M NaOH was used to adjust the pH to 8.5, and the resulting mixture was stirred overnight at room temperature. Subsequently, 1.0 M HCl was used to adjust the pH of the mixed solution to 3.5, the mixed solution was placed in a dialysis membrane with a molecular weight cutoff of 10,000, and dialysis was performed for 3 days in an HCl aqueous solution with a pH of 3.5 to remove any unreacted material and DDT. Freeze vacuum drying was then performed to obtain the thiol group-modified gelatin (Gela-SH). Estimating the thiol group modification rate using Ellman's reagent yielded a result of 0.45 mmol-SH/g-gelatin.

[Evaluation of Equilibrium Swelling Ratio ($Q_M$) and Gel Content]

The 4-arm PEG-SH, tyramine hydrochloride and the Gela-SH were each dissolved in PBS (pH 7.4). Next, 100 µL of the 4-arm PEG-SH aqueous solution, 100 µL of the Gela-SH aqueous solution and 50 µL of the tyramine aqueous solution were added to a mold, 50 µL of an HRP aqueous solution was then added, and the resulting mixture was left to stand for 4 hours at room temperature to produce a (PEG-SH)-(Gela-SH) hydrogel. The thus produced hydrogel was immersed in 10 mL of PBS (0.1% (w/v) sodium azide) for 4 days in an environment at 37° C., and the weight of the hydrogel after swelling ($M_S$) was measured. Subsequently, the hydrogel was dried, the dry weight of the hydrogel ($M_D$) was measured, and the equilibrium swelling ratio ($Q_M=M_S/M_D$) was calculated. Further, production of the gel was performed so as to achieve the final concentrations for each of the components shown in Table 6.

TABLE 6

| Samples | PEG-SH [% (w/v)] | Gela-SH [% (w/v)] |
| --- | --- | --- |
| P5G0 | 5 | 0 |
| P5G0.01 | 5 | 0.01 |
| P5G0.1 | 5 | 0.1 |
| P2.5G0.1 | 2.5 | 0.1 |
| P10G0.1 | 10 | 0.1 |

The gel content is an indicator that shows the degree of crosslinking of the polymer after gel production. First, the 4-arm PEG-SH, the Gela-SH (polymer weight: $W_p$) were each dissolved in PBS, and a (PEG-SH)-(Gela-SH) hydrogel was produced in the same manner as that described above. The produced gel was immersed in 10 mL of Milli-Q water for 4 days, and following removal of the non-crosslinked polymer, the gel was dried, the weight ($W_D$) was measured, and the gel content (=($W_D/W_p$)×100) was calculated.

[Evaluation of Mechanical Properties Using Rheometer]

The (PEG-SH)-(Gela-SH) hydrogel was produced inside an aluminum cup designed for a rheometer. The frequency was changed from 0.1 to 10 Hz, and the storage modulus (G') of each hydrogel was measured. The strain was 0.1%. Further, the concentrations of the various components were set to the same values as Example 7.

(Results and Observations)

Figure 14:
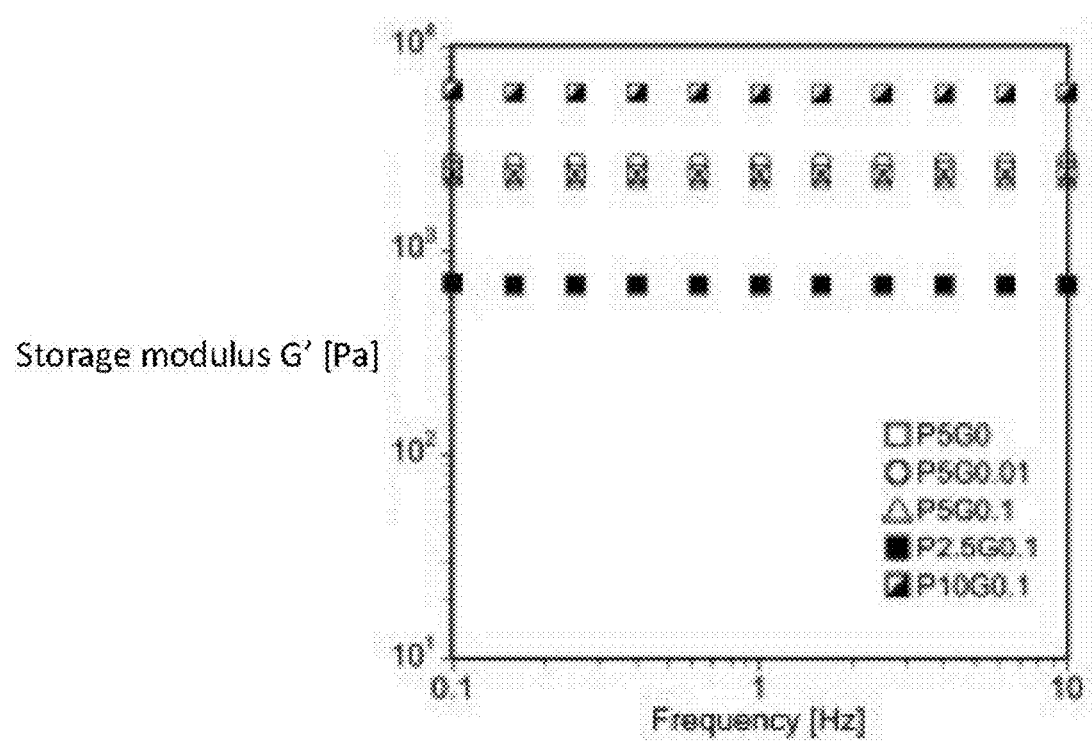
FIG. 14 is a diagram illustrating the storage modulus (G') of a (PEG-SH)-(Gela-SH) hydrogel in Example 12.

The equilibrium swelling ratio ($Q_M$) values of the hydrogels are shown in Table 7, and the storage modulus (G') values are shown in FIG. 14. As the concentration of the PEG-SH increased, the equilibrium swelling ratio of the hydrogel decreased and the storage modulus increased. In general, these properties reflect the crosslinking density between polymer molecules, with a higher crosslinking density resulting in a reduced equilibrium swelling ratio and an increased storage modulus. The production conditions for the gels in this example yielded a gel content of at least 80% in all of the gels, indicating that the crosslinking reaction between the polymer molecules had progressed significantly. Further, the thiol group concentration in the mixed solution increased as the PEG-SH concentration increased, and it is assumed that this is also a reason for the increase in the crosslinking density of the obtained hydrogel. It is thought that these reasons resulted in the results described above.

On the other hand, the equilibrium swelling ratio and the storage modulus of the hydrogel produced under conditions of 5% (w/v) PEG-SH were independent of the Gela-SH concentration, with similar values being obtained (see Table 7, FIG. 14). This means that the crosslinking densities of the produced hydrogels are essentially equal. In actual fact, in this example, the Gel-SH concentration was set to a comparatively low value compared with the PEG-SH concentration, meaning the thiol group concentration within the mixed solution did not change significantly with changes in the Gela-SH concentration (see Table 8). Accordingly, it was evident that under conditions of a low Gela-SH concentration, the physical properties of the obtained hydrogel were dependent on the concentration of the PEG-SH, meaning the physical properties can be easily controlled.

TABLE 7

| Samples | $Q_M$ [—] | Gel content [%] |
| --- | --- | --- |
| P5G0 | 41.1 ± 1.4 | 81.5 ± 2.6 |
| P5G0.01 | 39.6 ± 0.3 | 84.6 ± 1.0 |
| P5G0.1 | 39.1 ± 1.0 | 85.0 ± 2.6 |
| P2.5G0.1 | 64.2 ± 5.9 | 82.1 ± 4.9 |
| P10G0.1 | 33.6 ± 0.6 | 88.9 ± 1.2 |

TABLE 8

| Samples | Thiol group concentration [mM] |
| --- | --- |
| P5G0 | 10 |
| P5G0.01 | 10.045 |
| P5G0.1 | 10.45 |

[Cell Adhesion]

Aqueous solutions of the 4-arm PEG-SH, tyramine hydrochloride, HRP and the Gela-SH were mixed, and 500 µL samples of the mixed solution were added to a 12-well plate dish. Following gelation, the gel was washed twice with 1 mL samples of PBS, and then washed twice with MEM medium. Each well was inoculated with L292 fibroblasts at a rate of 2×10⁵ cells/well. Four hours after inoculation, each gel sheet was washed, and the cells within the supernatant liquid were collected. Further, 500 µL of a trypsin solution was added to each well, and the adhered cells were stripped and collected. The numbers of cells in the supernatant liquid and the trypsin-treated suspension were counted, and based on these values, the cell adhesion rate 4 hours after inoculation was calculated. Further, a similar investigation was performed using a gelatin-coated dish as a positive control.
[Cell Proliferation and Cell Sheet Production]

Gel sheets were produced in a 12-well plate dish using the same procedure as described above. Each well was inoculated with L292 fibroblasts at a rate of 2×10$^4$ cells/well. Three days after inoculation and 5 days after inoculation, each gel sheet was washed, and 500 µL of a trypsin solution was added to each well. Following collection of the adhered cells, a cell count was performed, and the number of cells in each well was calculated. Further, in this example, a similar investigation was performed using a gelatin-coated dish as a positive control. Cells were cultured on the (PEG-SH)-(Gela-SH) gel until confluency, and then 5 mL of a 10 mM cysteine solution was added to each well, and the wells were incubated for 30 minutes.
(Results and Observations)

Figure 15:
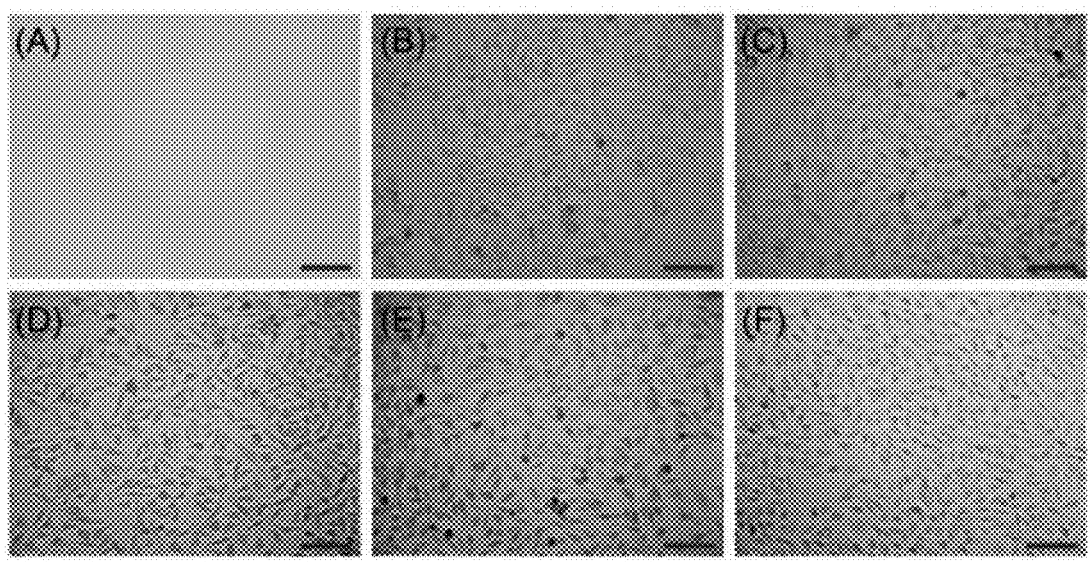
FIG. 15 shows microscope photographs from Example 12 of L929 fibroblasts 4 hours after inoculation on (A) P5G0, (B) P5G0.01, (C) P5G0.1, (D) P2.5G0.1, (E) P10G0.1, and (F) a gelatin-coated dish. The lines on the photographs indicate 100 μm.
Figure 16:
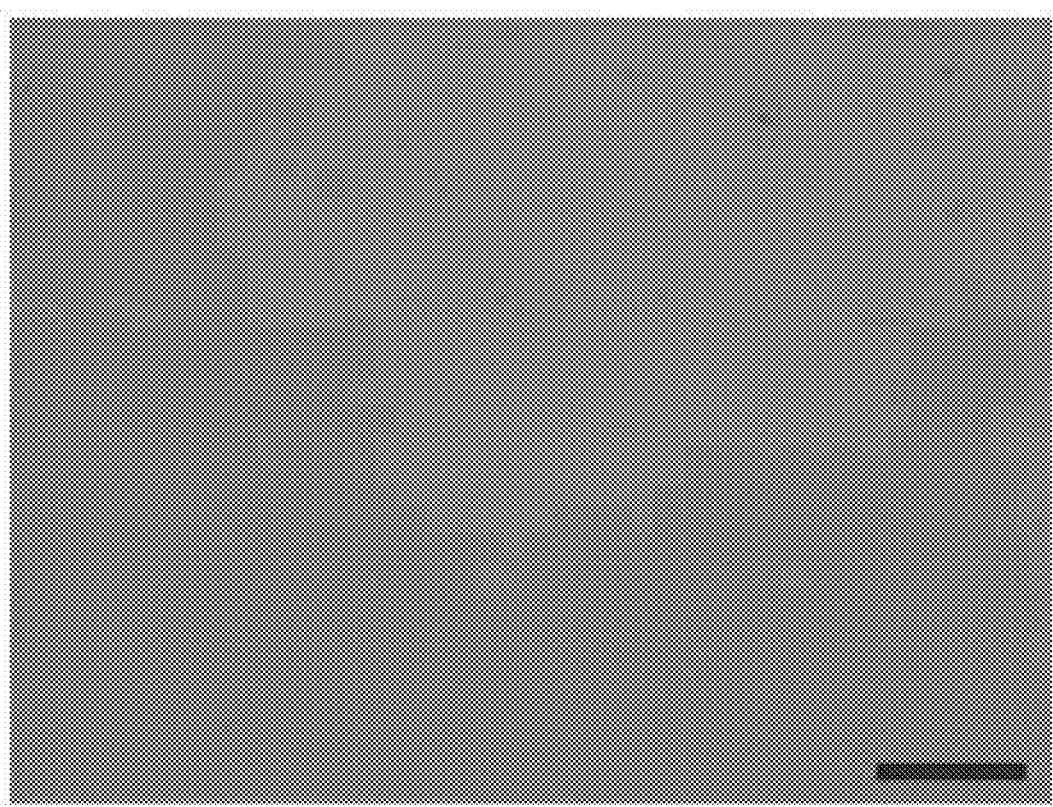
FIG. 16 is a microscope photograph from Example 12 of L929 fibroblasts 4 hours after inoculation on a hydrogel produced from 5% (w/v) PEG-SH and 0.1% (w/v) gelatin. The line on the photograph indicates 100 μm.
Figure 17:
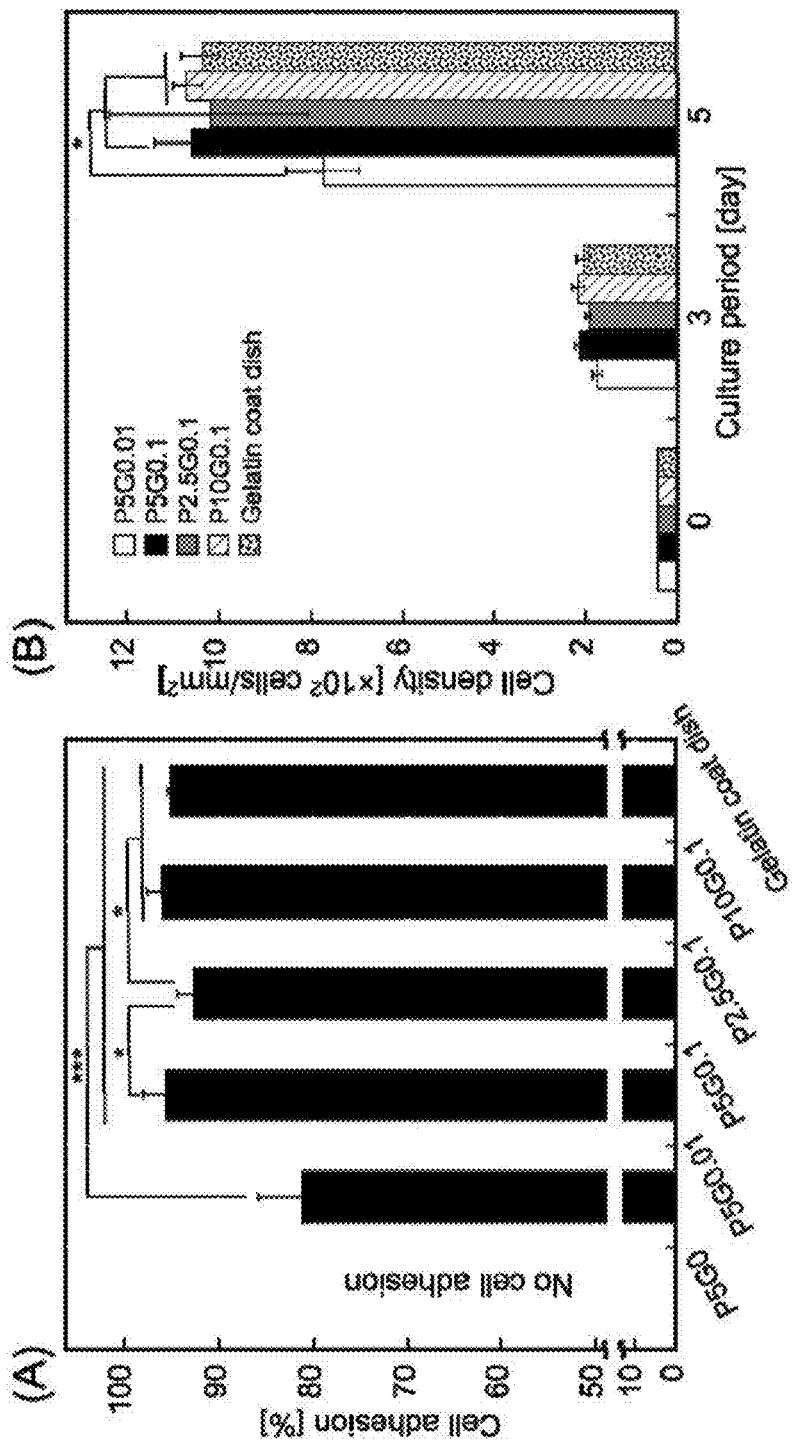
FIG. 17 is a series of diagrams from Example 12 illustrating (A) the cell adhesion and (B) the cell density of L929 fibroblasts on a (PEG-SH)-(Gela-SH) hydrogel. The error bars indicate standard deviations (SD) ((A): n=6, (B): n=3 (*p<0.05 and ***p<0.001)).

Microscope photographs of the L929 fibroblasts four days after inoculation are shown in FIG. 15. Adhesion and spreading of the cells was observed on the (PEG-SH)-(Gela-SH) gel sheet, but no cell adhesion was observed under conditions in which no Gela-SH was included in the mixture (see FIG. 15(A)). Further, a similar investigation was performed using a gelatin that had not been modified with thiol groups, but almost no cell adhesion was observed (see FIG. 16). This result shows that the Gela-SH was incorporated within the PEG-SH network via an HRP-catalyzed reaction, and indicates that other functional molecules (such as polysaccharides and peptides) can also be immobilized within the PEG gel using a similar procedure. As a result of calculating the cell adhesion rate after 4 hours from the cell numbers within the supernatant solution and on the gel, it was evident that the adhesion rate increased as the Gela-SH concentration increased (see FIG. 17(A)). Further under conditions including a Gela-SH concentration of 0.1% (w/v), at least 95% of the inoculated cells underwent adhesion, which was a similar result to the gelatin-coated dish of the positive control. Further, the cell count on the P5G0.1 hydrogel after 5 days culturing increased 40% compared with the cell count on the P5G0.01 hydrogel (see FIG. 17(B)). This means that the proliferation rate for the cells on the P5G0.1 hydrogel was faster than that on the P5G0.01 hydrogel. Further, it is also evident from the photographs of the form of the cells after 5 days culturing that the cell density on the P5G0.1 hydrogel was higher than that on the P5G0.01 hydrogel (see FIGS. 18(B) and (D)), indicating that the proliferation rate for the cells on the P5G0.1 hydrogel was faster than that on the P5G0.01 hydrogel. Furthermore, the proliferation rate and the form of the cells on the P5G0.1 hydrogel were similar to those on the gelatin-coated dish.

Further, under conditions where the PEG-SH concentration was changed, cell adhesion of at least 90% was achieved under all conditions. However, the cell adhesion rate on the gel produced at 2.5% (w/v) PEG-SH was slightly lower than that observed on the other gels (see FIG. 17(A)). It is thought that this is due to the strength of the gel. It has been reported that the adhesion of fibroblasts is promoted on substrates of higher strength. Similarly, in this example, it is thought that the fact that the G' value for the P2.5G0.1 hydrogel was about 1/10 that of the P10G0.1 hydrogel indicates that the strength of the substrate is affecting the adhesion. However, no significant difference was observed in terms of the proliferation rate, indicating that a small difference in the initial adhesion rate had no great effect on the cell proliferation rate.

Cells were cultured on the P5G0.1 gel sheet until confluency, and then a 10 mM cysteine solution was added. Subsequent incubation for 30 minutes yielded the cell sheets shown in FIGS. 19 (A) and (B). The obtained cell sheets were then transferred to a cell culture dish. After culturing overnight, a double staining kit was used to classify viable cells and dead cells by staining (wherein green indicates a viable cell and red indicates a dead cell). Fluorescence microscope photographs following the staining are shown in FIGS. 19(D) and (F), and FIG. 20(B). Almost no dead cells were observed, indicating that the cell sheet collection operation was extremely mild on the cells.

SEQUENCE LISTINGS

The invention claimed is:

1. A method for producing a hydrogel, comprising:
   forming a mixture including a polyethylene glycol having two or more thiol groups and a phenol compound; and
   adding peroxidase to the mixture to crosslink the polyethylene glycol having two or more thiol groups, in presence of the phenol compound, and produce the hydrogel.

2. The method for producing a hydrogel according to claim 1, wherein the peroxidase is a peroxidase derived from horseradish.

3. The method for producing a hydrogel according to claim 1, wherein the phenol compound is at least one of tyramine hydrochloride, phenol, N-lycyl-L-tyrosine, hydroquinone, resorcinol, catechol and serotonin.

4. The method for producing a hydrogel according to claim 1, wherein the polyethylene glycol having two or more thiol groups and a thiol compound having one or more thiol groups are crosslinked using the peroxidase in presence of the phenol compound.

5. The method for producing a hydrogel according to claim 1, wherein the polyethylene glycol having two or more thiol groups and a phenol compound having one or more thiol groups are crosslinked using the peroxidase.

6. A method for enveloping an envelopment target, comprising:

forming a mixture including a polyethylene glycol having two or more thiol groups and a phenol compound; and adding peroxidase to crosslink the polyethylene glycol having two or more thiol groups, in presence of the phenol compound, and produce a hydrogel to envelop the envelopment target in the hydrogel.

7. A method for releasing an envelopment target, comprising:

(a) applying a reducing agent to dissolve a hydrogel enveloping an envelopment target, the hydrogel having been produced by forming a mixture including a polyethylene glycol having two or more thiol groups and a phenol compound, and adding peroxidase to crosslink the polyethylene glycol having two or more thiol groups, in presence of the phenol compound, and produce the hydrogel; and (b) releasing the envelopment target after the hydrogel is dissolved in (a).

* * * * *